(12) United States Patent
Pasquier et al.

(10) Patent No.: US 9,062,207 B2
(45) Date of Patent: Jun. 23, 2015

(54) POLYCYCLIC AROMATIC HYDROCARBON COMPOUNDS CONTAINING AN S ATOM OR S(=O)$_2$ GROUP IN THEIR BASIC STRUCTURE

(71) Applicant: SICPA HOLDING SA, Prilly (CH)

(72) Inventors: Cécile Pasquier, Marly (CH); Patrick Wyss, Romont (CH)

(73) Assignee: SICPA HOLDING SA, Prilly (CH)

( * ) Notice: Subject to any disclaimer, the term of this patent is extended or adjusted under 35 U.S.C. 154(b) by 156 days.

(21) Appl. No.: 13/683,622

(22) Filed: Nov. 21, 2012

(65) Prior Publication Data

US 2013/0127150 A1 May 23, 2013

Related U.S. Application Data

(60) Provisional application No. 61/563,381, filed on Nov. 23, 2011.

(30) Foreign Application Priority Data

Nov. 23, 2011 (EP) .................. PCT/EP2011/070869

(51) Int. Cl.
  *C09B 57/08* (2006.01)
  *C07D 495/16* (2006.01)
  *C09B 5/62* (2006.01)

(52) U.S. Cl.
  CPC . *C09B 57/08* (2013.01); *C09B 5/62* (2013.01); *C07D 495/16* (2013.01)

(58) Field of Classification Search
  CPC ...................................................... C09B 57/08
  USPC ............ 528/373, 377; 283/67, 81; 106/31.13; 252/500; 524/611; 546/31, 47
  See application file for complete search history.

(56) References Cited

U.S. PATENT DOCUMENTS

| | | |
|---|---|---|
| 3,367,937 A | 2/1968 | Fuchs et al. |
| 3,502,678 A | 3/1970 | Otto et al. |
| 4,911,731 A | 3/1990 | Loveless et al. |
| 5,030,697 A | 7/1991 | Hugl et al. |
| 5,151,516 A | 9/1992 | Beck et al. |
| 6,277,536 B1 | 8/2001 | Piastra et al. |
| 6,727,318 B1 | 4/2004 | Mathauer et al. |
| 7,582,150 B2 | 9/2009 | Jaunky et al. |
| 7,582,151 B2 | 9/2009 | Jaunky et al. |
| 7,582,152 B2 | 9/2009 | Jaunky et al. |
| 7,795,431 B2 | 9/2010 | Pschirer et al. |
| 7,812,113 B2 | 10/2010 | Deroover et al. |
| 7,846,992 B2 | 12/2010 | Deroover et al. |
| 8,231,809 B2 | 7/2012 | Pschirer et al. |
| 2002/0112297 A1 | 8/2002 | Kaul et al. |
| 2002/0182422 A1 | 12/2002 | Garrett et al. |
| 2004/0194665 A1 | 10/2004 | Konemann et al. |
| 2006/0058330 A1 | 3/2006 | Krieger et al. |
| 2008/0245411 A1 | 10/2008 | Hammermann et al. |
| 2008/0282481 A1 | 11/2008 | De Boni et al. |
| 2009/0056793 A1 | 3/2009 | Langhals et al. |
| 2009/0255063 A1 | 10/2009 | Marquais-Bienewald et al. |
| 2010/0011656 A1 | 1/2010 | Gessner et al. |
| 2011/0293899 A1 | 12/2011 | Tiller et al. |
| 2012/0299286 A1 | 11/2012 | Tiller et al. |

FOREIGN PATENT DOCUMENTS

| | | |
|---|---|---|
| DE | 198 05 121 A1 | 8/1999 |
| DE | 10 2008 036495 | 2/2010 |
| EP | 0 361 229 A | 4/1990 |
| EP | 0 422 535 A1 | 4/1991 |
| EP | 0 999 239 A2 | 5/2000 |
| EP | 1 172 418 A2 | 1/2002 |
| FR | 1 444 489 A | 7/1966 |
| FR | 1 489 487 A | 7/1967 |
| FR | 2 194 828 A1 | 3/1974 |
| FR | 2 850 651 A1 | 8/2004 |
| GB | 1436903 | 5/1976 |
| WO | 99/24527 A1 | 5/1999 |
| WO | 2006/097360 | 9/2006 |
| WO | 2007/006634 | 1/2007 |
| WO | 2007/006682 | 1/2007 |
| WO | 2008/001036 | 1/2008 |
| WO | 2008/009579 A1 | 1/2008 |
| WO | 2012/160182 | 11/2011 |
| WO | 2011/147857 | 12/2011 |

OTHER PUBLICATIONS

U.S. Appl. No. 13/673,418 claims (Nov. 2012).*
Shirosaki et al., "Dyes for hydrophobic fibers XP002678127", Database CA [Online] Chemical Abstracts Service, Columbus Ohio, US, 1976, PP.
Miura et al., "Liquid crystal compositions XP002678128", Database CA [Online] Chemical Abstracts Service, Columbus Ohio, US, 1986, PP.
Imahori et al., "Benzothioxanethene dyes for polyester fibers XP002678129", Database CA [Online] Chemical Abstracts Service, Columbus Ohio, US, 1976, PP.
Imahori et al., "Coloring organic polymer materials XP002678130", Database CA [Online] Chemical Abstracts Service, Columbus Ohio, US, 1976, PP.
Toba et al., "Holographic recording material with chemical and environmental stability and manufacture of volume phase-type hologram by using same XP002678131", Database CA [Online] Chemical Abstracts Service, Columbus Ohio, US, 1995, PP.
Yamaoka et al., "Polymerizable resin compositions XP002678132", Database CA [Online] Chemical Abstracts Service, Columbus Ohio, US, 1986, PP.
Enokida et al., "Organic electroluminescent devices XP002678126", Database CA [Online] Chemical Abstracts Service, Columbus Ohio, US, 1995, PP.

(Continued)

*Primary Examiner* — Duc Truong
(74) *Attorney, Agent, or Firm* — Greenblum & Bernstein, P.L.C.

(57) ABSTRACT

Polycyclic aromatic hydrocarbon compounds having an S atom or S(=O)$_2$ moiety incorporated in their basic polycyclic structure that can have a nitrogen-containing heterocycloaliphatic group and/or a substituted or unsubstituted phenoxy group and/or a polymeric moiety bonded to the polycyclic structure and to compositions such as, e.g., printing inks which comprise these polycyclic aromatic hydrocarbons as colorants.

32 Claims, No Drawings

(56) References Cited

OTHER PUBLICATIONS

Marechal, "Polymeric Dyes—Synthesis, Properties and Uses", Progress in Organic Coatings, vol. 10, 1982, pp. 251-287.
Guthrie, "Polymeric Colorants", Review of Progress in Coloration, Society of Dyers and Clourists, Bradford, GB. vol. 20, Jan. 1, 1990, pp. 40-52.
U.S. Appl. No. 13/673,418 to Cecile Pasquier et al., which was filed on Nov. 9, 2012.
Search Report and Written Opinion for. PCT/EP2011/069885, mailed Jun. 27, 2012.
Search Report and Written Opinion for PCT/EP2011/070869, mailed Jul. 2, 2012.
Search Report and Written Opinion for. PCT/EP2011/058519, mailed Feb. 8, 2011.
Search Report and Written Opinion for. PCT/EP2012/059795, mailed Jun. 29, 2012.
Chinese Office Action with English Translation in respect to Chinese Application No. 201280024816.7, dated Aug. 27, 2014.

* cited by examiner

POLYCYCLIC AROMATIC HYDROCARBON COMPOUNDS CONTAINING AN S ATOM OR S(=O)₂ GROUP IN THEIR BASIC STRUCTURE

CROSS-REFERENCE TO RELATED APPLICATIONS

The present application claims the benefit under 35 U.S.C. §119(e) of U.S. Provisional Application No. 61/563,381, filed Nov. 23, 2011 and claims priority under 35 U.S.C. §119 of International Patent Application No. PCT/EP2011/070869, filed Nov. 23, 2011. The entire disclosures of these applications are expressly incorporated by reference herein.

BACKGROUND OF THE INVENTION

1. Field of the Invention

The present invention relates to novel polycyclic aromatic hydrocarbon compounds having an S atom or S(=O)₂ moiety incorporated in their basic polycyclic structure that can have a nitrogen-containing heterocycloaliphatic group and/or a substituted or unsubstituted phenoxy group and/or a polymeric moiety bonded to the polycyclic structure and to compositions such as, e.g., printing inks which comprise these polycyclic aromatic hydrocarbons as colorants.

2. Discussion of Background Information

Counterfeiting and market diversion of mass produced goods are facilitated if the products are handled on a lot base rather than on an individual item base. In such case counterfeit or diverted products are easily introduced into the supply chain. Producers and retailers would like to be in a position to distinguish their original products from such counterfeit or diverted (parallel imported or smuggled) products at the level of the individual unit that is sold.

Further, secure documents such as currency, passports, or identity cards are increasingly counterfeit around the world. This situation is a very critical issue for governments and society in general. For example criminal organizations may use fake passports or identity cards for human beings traffic. As reprographic technologies become more and more sophisticated, it becomes even more difficult to make a clear distinction between a fake document and the original. Document security has therefore a considerable impact on the economy of the countries and also on the victims of illicit traffic involving counterfeit documents.

In an attempt to prevent counterfeiting marking is currently used extensively for the recognition, identification and authentication of individual items. The marking may be applied, for example, in the form of indicia such as 1-dimensional barcodes, stacked 1-dimensional barcodes, 2-dimensional barcodes, 3-dimensional barcodes, a data matrix. and the like. The application of markings is frequently carried out by a printing process which uses a printing ink with specific optical properties that are imparted to the ink by one or more substances contained therein such as, e.g., luminescent dyes, pigments, or cholesteric liquid crystal compounds.

A class of compounds which is suitable for use in, e.g., printing inks for marking purposes are compounds having a perylene, terrylene or quaterrylene skeleton. Perylene, terrylene and quaterrylene display fluorescence and there are many derivatives of these compounds which are known and may theoretically be employed as pigments in compositions for marking such as printing inks and the like. However, a drawback of these compounds is their often unsatisfactorily low solubility or dispersibility in liquid media such as those which are useful in printing inks. This low solubility/dispersibility limits the suitability of these compounds as colorants for liquid compositions in general. It would thus, be advantageous to be able to increase the solubility and/or dispersibility of perylene, terrylene and quaterrylene dyes in liquid media and in particular, liquid media for use in printing inks. See application Ser. No. 13/115,602, filed May 25, 2011, and Provisional Application No. 61/558,236, filed Nov. 10, 2011 which are incorporated by reference herein in their entireties.

SUMMARY OF THE INVENTION

The present invention provides polycyclic aromatic hydrocarbon compounds of general formula (1):

wherein P represents a polymeric moiety having at least three repeating units which comprise an optionally substituted phenyl ring;

Q represents a polycyclic aromatic hydrocarbon moiety containing an S atom or S(=O)₂ moiety (i.e., a polycyclic aromatic hydrocarbon skeleton having an S atom or a S(=O)₂ moiety incorporated in its basic structure which may optionally comprise one or more substituents in addition to the substituents Y and/or P—O);

Y is selected from (i) halogen, (ii) optionally substituted N-heterocycloaliphatic groups having from 3 to about 8 ring members and which are bonded to Q through an N atom, and (iii) optionally substituted phenoxy groups;

x represents an integer of from 0 to 4; and w represents an integer of from 0 to 4, and wherein w and x are not simultaneously 0, provided that when x=0, at least one Y is selected from (ii) and (iii).

In one aspect of the compound of formula (1), x may be 1 and/or (x+w) may not be higher than about 6.

In another aspect, Q may be a moiety having a basic structure (i.e., without optionally present substituents) of formula (A) or (B) or (A') or (B'):

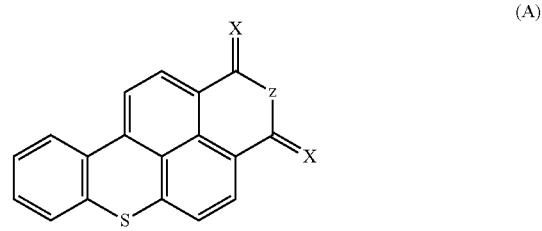

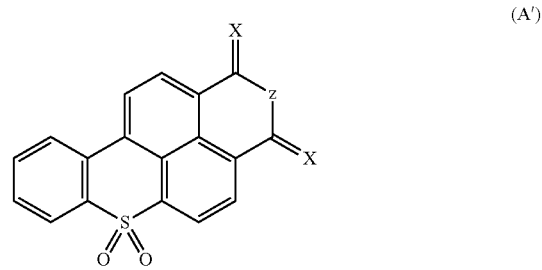

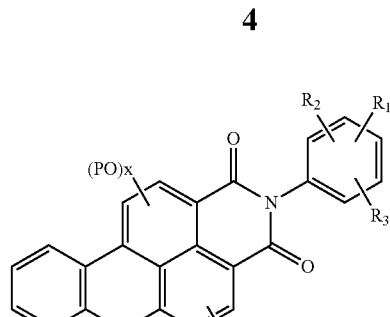

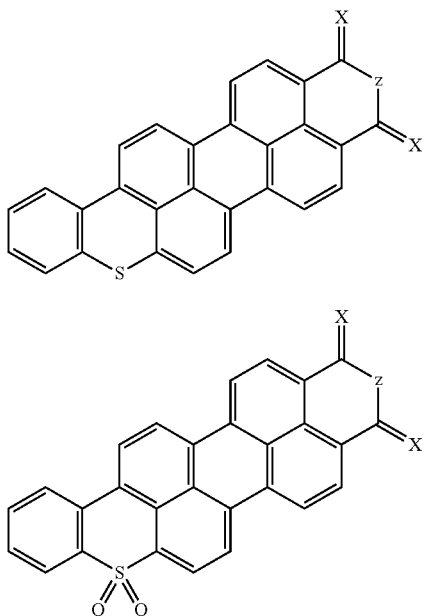

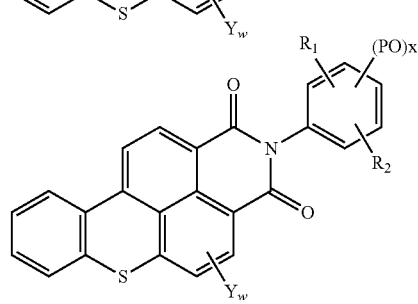

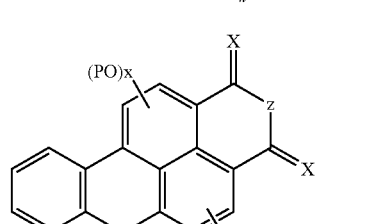

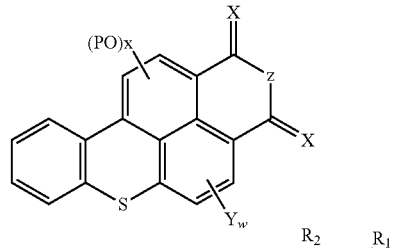

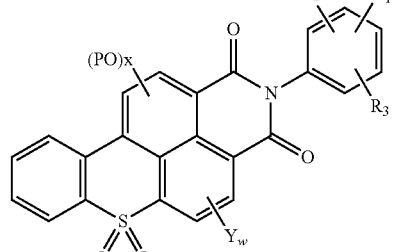

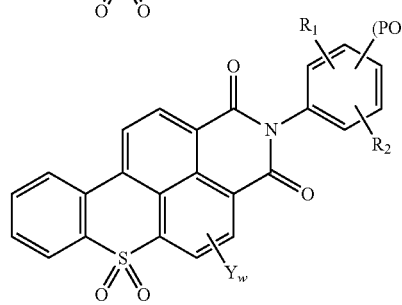

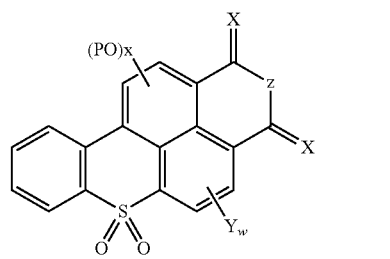

wherein Z represents O, S or N—R, and X, which can be the same or different, represents O, S, or NR'. Thus, the group formed by Z and X can be represented, for example, by —CO—Z—O— (may be replaced by [—COOH HOOC—] (i.e., the dicarboxylic acid instead of the anhydride)), —CS—Z—CO—, —CS—Z—CS—, or —C(=NR')—NR—CO—; and
R and R' independently represent an optionally substituted aliphatic, cycloaliphatic, aromatic, heteroaromatic, alkylaryl, alkylheteroaryl, arylalkyl or heteroarylalkyl group having from 1 to about 20 carbon atoms; and R and R' may also be combined to form, together with the N atoms to which they are attached, an optionally substituted and/or fused 5- to 7-membered ring.

In one aspect of the compounds of the above formulae (A), (B), (A') and (B'), for the group Z=N—R, R may be selected, for example, from optionally substituted alkyl having from 1 to about 6 carbon atoms, optionally substituted alkylaryl or arylalkyl having from 7 to about 12 carbon atoms, optionally substituted aryl having from about 6 to about 20 carbon atoms, and optionally substituted heteroaryl having from about 3 to about 20 carbon atoms such as, e.g., from optionally substituted alkyl having from 1 to about 4 carbon atoms, optionally substituted phenyl, or optionally substituted benzyl. By way of non-limiting example, R may represent phenyl substituted with from 1 to about 3 groups selected from halogen and alkyl having from 1 to about 6 carbon atoms such as, e.g., a phenyl group substituted by at least two alkyl groups which comprise a secondary or tertiary carbon atom, examples of which include isopropyl and tert.-butyl groups.

In another aspect of the compounds of the above formulae (A), (B), (A') and (B'), the group Z represents O or N—R (including compounds wherein each group Z is O, compounds wherein each group Z is N—R (with the groups R being the same or different), and compounds wherein one group Z is O and the other group Z is N—R).

For example, compounds of the instant invention include compounds of formulae (I) or (II) or (III) or (IV) or (V) or (VI) which can include (PO)$_x$ and/or Y$_w$:

wherein in the case of formula (III) and (VI), the group Z, represents O, S or N—R, and X, which can be the same or different, represents O, S, or NR'. Thus, the group formed by Z and X can be represented, for example, by —CO—Z—O— (may be replaced by [—COOH HOOC—] (i.e., the dicarboxylic acid instead of the anhydride)), —CS—Z—O—, —CS—Z—CS—, or —C(=NR')—NR—CO—;

R and R' independently represent an optionally substituted aliphatic, cycloaliphatic, aromatic, heteroaromatic, alkylaryl, alkylheteroaryl, arylalkyl or heteroarylalkyl group having from 1 to about 20 carbon atoms; and R and R' may be combined to form, together with the N atoms to which they are attached, an optionally substituted and/or fused 5- to 7-membered ring;

$R_1$, $R_2$ and $R_3$ are independently selected from hydrogen, $C_1$-$C_4$ alkyl, $C_1$-$C_4$ alkyl-COOH, $C_1$-$C_4$ alkyl-$SO_3H$, $C_1$-$C_4$ alkoxy, mono($C_1$-$C_4$)alkylamino, di($C_1$-$C_4$)alkylamino, $C_1$-$C_4$ aminoalkyl, halogen, cyano, nitro, and $SO_3H$, the alkyl groups being optionally substituted;

Y is selected from (i) halogen, (ii) optionally substituted N-heterocycloaliphatic groups having from 3 to about 8 ring members and which are bonded to an aromatic ring through an N atom, (for example, at least one group Y may be selected from heterocycloaliphatic groups having from 3 to about 8 ring members, which ring members may comprise from 1 to about 3 heteroatoms (e.g., 1, 2 or 3 heteratoms) selected from N, S, and O, provided that at least one ring member is N and/or the heterocycloaliphatic groups may be substituted by one or more substituents selected from alkyl and alkoxy groups comprising up to about 10 carbon atoms) and (iii) optionally substituted phenoxy groups which are bonded to an aromatic ring through an O atom, the phenoxy group may be substituted by one or more (e.g., 1, 2 or 3 identical or different) substituents selected from halogen (e.g., F, Cl, Br and I), nitro, cyano, NRR', $SO_3H$ and COOH and salts and derivatives of these sulfonic and carboxylic acid groups (e.g., salts of alkali and alkaline earth metals such as Na, K, Ca, and Mg, esters such as C1-C4 alkyl esters, and amides such as amides with NRR' as amido moiety), OH, heterocycloalkyl comprising up to three heteroatoms selected from O, N and S as ring members and from 3 to about 8 ring members, and alkyl (including cycloalkyl) and alkoxy (including cycloalkoxy) groups comprising from 1 to about 10 carbon atoms (e.g., 1, 2, 3, 4, 5 or 6 carbon atoms);

P represents a polymeric moiety having at least three repeating units which comprise an optionally substituted phenyl ring;

and x is an integer of from 0 to 4, w is an integer of from 0 to 4.

In yet another aspect of the compounds of the present invention, Q may be a moiety having a basic structure (i.e., without optionally present substituents) of formula (C) or (D) or (E) or (F) or (G) or (H) which can include $(PO)_x$ and/or $Y_w$:

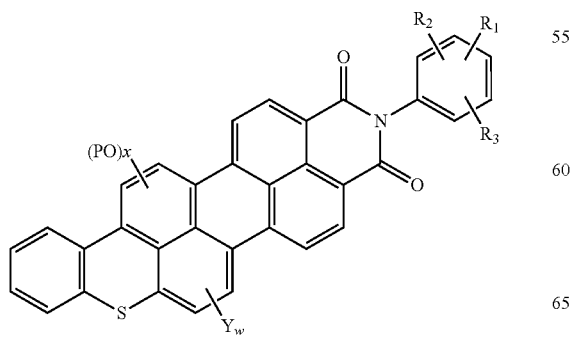

(C)

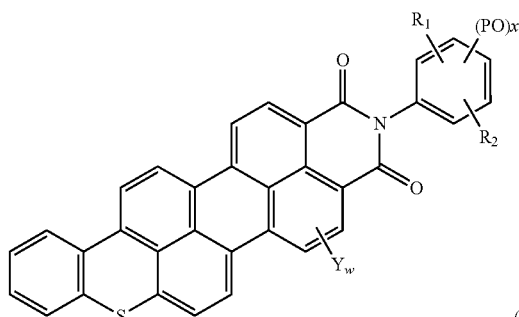

(D)

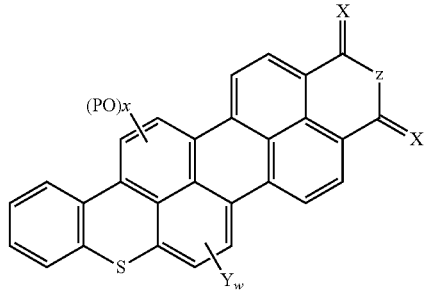

(E)

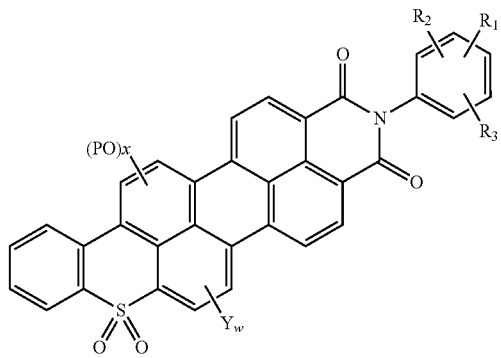

(F)

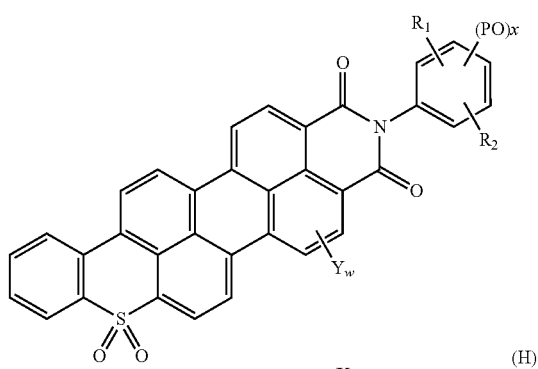

(G)

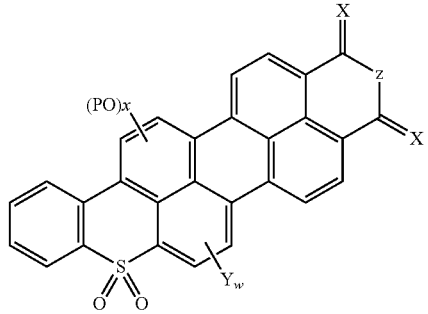

(H)

wherein in the case of formula (E) and (H), Z represents O, S or N—R, and X, which can be the same or different, represents O, S, or NR'. Thus, the group formed by Z and X can be represented, for example, by —CO—Z—CO— (may be replaced by [—COOH HOOC—] (i.e., the dicarboxylic acid instead of the anhydride)), —CS—Z—CO—, —CS—Z—CS—, or —C(=NR')—NR—CO—;

R and R' independently represent an optionally substituted aliphatic, cycloaliphatic, aromatic, heteroaromatic, alkylaryl, alkylheteroaryl, arylalkyl or heteroarylalkyl group having from 1 to about 20 carbon atoms; and R and R' may be combined to form, together with the N atoms to which they are attached, an optionally substituted and/or fused 5- to 7-membered ring;

$R_1$, $R_2$ and $R_3$ are independently selected from hydrogen, $C_1$-$C_4$ alkyl, $C_1$-$C_4$ alkyl-COOH, $C_1$-$C_4$ alkyl-$SO_3H$, $C_1$-$C_4$ alkoxy, mono($C_1$-$C_4$)alkylamino, di($C_1$-$C_4$)alkylamino, $C_1$-$C_4$ aminoalkyl, halogen, cyano, nitro, and $SO_3H$, the alkyl groups being optionally substituted;

Y is selected from (i) halogen, (ii) optionally substituted N-heterocycloaliphatic groups having from 3 to about 8 ring members and which are bonded to an aromatic ring through an N atom; (for example, at least one group Y may be selected from heterocycloaliphatic groups having from 3 to about 8 ring members, which ring members may comprise from 1 to about 3 heteroatoms (e.g., 1, 2 or 3 heteroatoms) selected from N, S, and O, provided that at least one ring member is N and/or the heterocycloaliphatic groups may be substituted by one or more substituents selected from alkyl and alkoxy groups comprising up to about 10 carbon atoms) and (iii) optionally substituted phenoxy groups which are bonded to an aromatic ring through an O atom, the phenoxy group may be substituted by one or more (e.g., 1, 2 or 3 identical or different) substituents selected from halogen (e.g., F, Cl, Br and I), nitro, cyano, NRR', $SO_3H$ and COOH and salts and derivatives of these sulfonic and carboxylic acid groups (e.g., salts of alkali and alkaline earth metals such as Na, K, Ca, and Mg, esters such as $C_1$-$C_4$ alkyl esters, and amides such as amides with NRR' as amido moiety), OH, heterocycloalkyl comprising up to three heteroatoms selected from O, N and S as ring members and from 3 to about 8 ring members, and alkyl (including cycloalkyl) and alkoxy (including cycloalkoxy) groups comprising from 1 to about 10 carbon atoms (e.g., 1, 2, 3, 4, 5 or 6 carbon atoms);

P represents a polymeric moiety having at least three repeating units which comprise an optionally substituted phenyl ring;

and x represents an integer of from 0 to 4; and w is an integer of from 0 to 4.

Thus, for formula (C) or (D) or (E) or (F) or (G) or (H), each of x and w can both be 0, either x and w can be 0, and x can be 0, 1, 2, 3 or 4, and w can be 0, 1, 2, 3 or 4.

Additionally, the present invention provides compounds of Formula (B) and (B') as set forth above that are completely unsubstituted or carry one or more (e.g., 1, 2, 3, 4, 5, or 6) substituents (which may be the same or different). Non-limiting examples of substituents include halogen (e.g., F, Cl, Br and I), nitro, cyano, NRR', $SO_3H$ and COOH and salts and derivatives of these sulfonic and carboxylic acid groups (e.g., salts of alkali and alkaline earth metals such as Na, K, Ca, and Mg, esters such as C1-C4 alkyl esters, and amides such as amides with NRR' as amido moiety), OH, heterocycloalkyl comprising up to three heteroatoms selected from O, N and S as ring members and from 3 to about 8 ring members, alkyl (including cycloalkyl) and alkoxy (including cycloalkoxy) groups comprising from 1 to about 10 carbon atoms (e.g., 1, 2, 3, 4, 5 or 6 carbon atoms), and optionally substituted aryl (e.g. phenyl) and aralkyl (e.g., benzyl) groups having up to about 20 carbon atoms.

In one aspect of these compounds of the present invention, the group Z represents N—R wherein R may be selected, for example, from optionally substituted alkyl having from 1 to about 6 carbon atoms, optionally substituted alkylaryl or arylalkyl having from 7 to about 12 carbon atoms, optionally substituted aryl having from about 6 to about 20 carbon atoms, and optionally substituted heteroaryl having from about 3 to about 20 carbon atoms such as, e.g., from optionally substituted alkyl having from 1 to about 4 carbon atoms, optionally substituted phenyl, or optionally substituted benzyl. By way of non-limiting example, R may represent phenyl substituted with from 1 to about 3 groups selected from halogen and alkyl having from 1 to about 6 carbon atoms such as, e.g., a phenyl group substituted by at least two alkyl groups which comprise a secondary or tertiary carbon atom, non-limiting examples of which include isopropyl and tert.-butyl groups.

In a still further aspect, at least one group Y of the compounds of disclosed herein, such as the compound of formula (1), may be selected from heterocycloaliphatic groups having from 3 to about 8 ring members, which ring members may comprise from 1 to about 3 heteroatoms (e.g., 1, 2 or 3 heteratoms) selected from N, S, and O, provided that at least one ring member is N. Further, the heterocycloaliphatic groups may be substituted by one or more substituents selected from alkyl and alkoxy groups comprising up to about 10 carbon atoms.

For example, at least one group Y of the compounds disclosed herein, such as the compound of formula (1) or the compounds of the other formulas, may be the residue (i.e., without a hydrogen atom bonded to the N atom) of a heterocyclic compound selected from optionally substituted azacyclooctane, optionally substituted azepane, optionally substituted piperidine, optionally substituted piperazine, optionally substituted pyrrolidine, optionally substituted azetidine, optionally substituted aziridine, optionally substituted morpholine, optionally substituted oxazolidine, optionally substituted pyrazolidine, optionally substituted isopyrazolidine, optionally substituted isoxazolidine, and optionally substituted thiazolidine. The optional substituents on the rings may preferably be independently selected from $C_1$-$C_4$ alkoxy and $C_1$-$C_6$ alkyl groups. Of course, a compound may comprise two or more different heterocycloaliphatic groups Y.

In a still further aspect, at least one group Y, when present, of the compounds disclosed herein, such as the compound of formula (1) or compounds of the other formulas, may be selected from optionally substituted phenoxy groups, wherein the phenoxy group may be substituted by one or more (e.g., 1, 2 or 3 identical or different) substituents selected from halogen (e.g., F, Cl, Br and I), nitro, cyano, NRR', $SO_3H$ and COOH and salts and derivatives of these sulfonic and carboxylic acid groups (e.g., salts of alkali and alkaline earth metals such as Na, K, Ca, and Mg, esters such as $C_1$-$C_4$ alkyl esters, and amides such as amides with NRR' as amido moiety), OH, heterocycloalkyl comprising up to three heteroatoms selected from O, N and S as ring members and from 3 to about 8 ring members, and alkyl (including cycloalkyl) and alkoxy (including cycloalkoxy) groups comprising from 1 to about 10 carbon atoms (e.g., 1, 2, 3, 4, 5 or 6 carbon atoms).

In another aspect of the compounds set forth above, P—O, when present, may be the residue (i.e., without hydrogen atom of one of the phenolic hydroxy groups) of a compound of general formula (2):

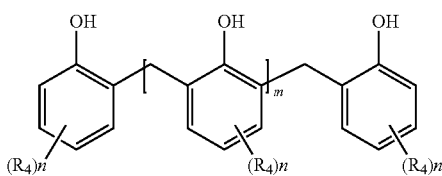

(2)

wherein the groups $R_4$, the same or different from each other, are selected from $C_1$-$C_{10}$ alkyl and $C_1$-$C_4$ alkoxy; m represents an integer of from 1 to about 30; and n represents an integer of from 1 to about 3. For example, m may represent an integer of from 1 to 10 and/or n may be 1 or 2 and/or the groups $R_4$ may independently be selected from $C_1$-$C_{10}$ alkyl such as, e.g., isopropyl, tert-butyl, tert-octyl, n-nonyl and branched nonyl.

The present invention also provides a process for making compounds disclosed herein, such as the compound of formula (1). The process comprises reacting in an aprotic polar organic solvent a compound of formula Q-(Hal)$_v$ wherein Hal represents halogen and v represents an integer of from 1 to 8, with an N-containing cycloaliphatic compound and/or a polymeric compound of formula P—OH and/or an optionally substituted phenolic compound. If two or more different compounds are to be reacted with a compound of formula Q-(Hal)$_v$ the reactions are preferably carried out successively (with or without isolating the intermediate) in order to be able to better control the composition of the mixture of reaction products obtained. One of skill in the art will appreciate that depending on the reaction conditions individual compounds or a mixture of positional isomers may be obtained if v is 2 or higher.

The process for preparing compounds Q-(Hal)$_v$ wherein Hal represents halogen and v represents an integer of from 1 to 8 may be performed as follows by reacting compounds Q as above-mentioned, such as represented by formula (A), (A'), (B) or (B') free of halogen. Q compounds can be reacted in AcOH as a solvent with about 5 equivalent of SO$_2$Cl$_2$ in the presence of I$_2$ and iodobenzene as catalyst, the whole composition can be heated between 70 to 90° C. during about three or to four hours or over night depending on the initial compounds used. The resulting mixtures can be washed with a mixture of water and organic solvent. The organic phase can be obtained after extraction of the organic solvent from water, the solvent can then be evaporated and the resulting crude oil can be subject to separation and purification with techniques of purification known by one skilled in the art, such as chromatography.

The process for preparing the molecule (A), (A'), (B) or (B') can comprise the following step (a) or (b):

(a)

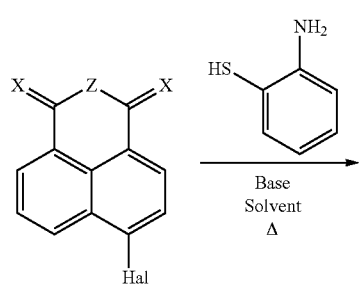

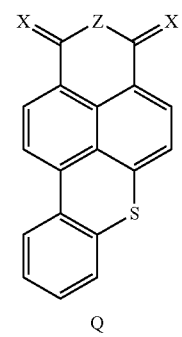

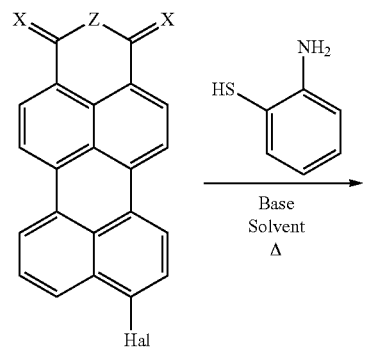

(b)

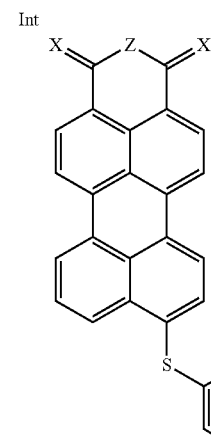

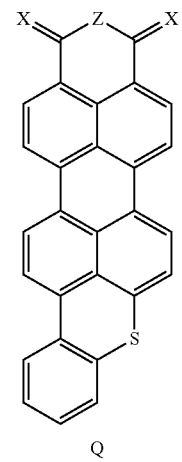

wherein X and Z are the same as above defined and Hal represents halogen such as Cl or Br, various bases can be used such as K$_2$CO$_3$ and the solvent is for example a polar solvent such as N-methyl-2-pyrrolidone (NMP). The temperature of reaction represented by Δ can be between 80 to 120° C., and the preparation of compounds Int (also named intermediate of synthesis leading to preparation of molecule Q) is well known by one skilled in the art or are also commercially available.

In one aspect of the process, at least the reaction involving the N-containing cycloaliphatic compound (and usually also the reaction involving the reaction comprising the polymeric compound and/or the optionally substituted phenolic compound) may be carried out in the presence of an inorganic base and/or a strong organic non-nucleophilic base.

In another aspect of the process, at least the reaction involving the optionally substituted phenolic compound (and usually also the reaction involving the reaction comprising the polymeric compound or the optionally phenolic compound) may be carried out in the presence of an inorganic base and/or a strong organic non-nucleophilic base.

In another aspect of the process, from about 0.5 to about 10 g of compound of formula Q-(Hal)$_v$ may be employed per 100 g of polymeric compound of formula P—OH. In another aspect of the process, from about 0.5 to about 10 g of compound of formula Q-(Hal)$_v$ may be reacted with from about 2 to 3 equivalent of optionally substituted phenolic compound. In another aspect of the process, from about 0.5 to about 10 g of compound of formula Q-(Hal)$_v$ may be reacted with 5 to 10 equivalents of N-containing cycloaliphatic compound or the reaction can be made for example with the N-containing cycloaliphatic compound as a co-solvent together with the one needed for carrying out the process according to the invention.

In yet another aspect, the polar solvent may comprise at least one solvent in which the polymeric compound, if used, is soluble and/or may be at least one of N-methylpyrrolidone, dimethyl formamide, dimethyl acetamide, and dimethylsulfoxide.

The present invention also provides a printing ink composition. The composition comprises a polar liquid medium and at least one compound of formula (1) or (A) or (A') or (B) or (B') or (C) or (D) or (E) or (F) or (G) or (H) or (I) or (II) or (III) or (IV) or (V) or (VI) disclosed herein, such as the compound of formula (1) or compounds of the other formulas dissolved or dispersed in the medium. Such medium for non limiting example may be methyl ethyl ketone (MEK) or dimethylketone.

In one aspect, the composition may comprise from about 0.01% to about 40%, e.g., from about 0.05% to about 10%, or from about 0.1% to about 5% by weight of at least one compound disclosed herein, such as the compound of formula (1) or compounds of the other formulas, based on the total weight of the composition In another aspect, the composition may further comprise at least one conductivity imparting substance (such as, e.g., a salt).

The present invention further provides a marking or security feature which is made with the printing ink composition of the present invention as set forth above and/or comprises at least one compound disclosed herein, such as the compound of formula (1) or compounds of the other formulas.

In one aspect, the marking or security feature may comprise at least one of a thread, a label, a barcode, a 2D code, a pattern, indicia, a data matrix, a stamp, a tax stamp, a stamp, a tax stamp, a digital stamp, and a cloud of dots (visible or invisible) which supports data information.

The present invention also provides an article which comprises the marking or security feature set forth above. For example, the marking or security feature may be present as a layer on the article.

In one aspect, the article may be at least one of a label such as, e.g., a tax label, packaging, a can, a metal, an aluminum foil, a cartridge, a closed cartridge (e.g., a capsule) that contains, e.g., a pharmaceutical, a nutraceutical, a foodstuff or a beverage (such as, e.g., coffee, tea, milk, chocolate, etc.), an article made of glass, an article made of ceramic, a banknote, a stamp, a security document, an identity card, a passport, a driver's license, a credit card, an access card, a ticket such as, e.g., a transportation ticket or an event ticket, a voucher, a value document, an ink-transfer film, a reflective film, a thread, a commercial good, and a cigarette packaging carrying or not carrying coded or encrypted information.

The present invention also provides a method of authenticating an article. The method comprises providing the article with the marking or security feature set forth above (including the various aspects thereof) and/or comprises applying onto the article the printing ink composition set forth above (including the various aspects thereof).

In one aspect of the method, the article may be at least one of a tax label, packaging, a can, a metal, an aluminum foil, a cartridge, a closed cartridge (e.g., a capsule) that contains, e.g., a pharmaceutical, a nutraceutical, a foodstuff or a beverage (such as, e.g., coffee, tea, milk, chocolate, etc.), an article made of glass, an article made of ceramic, a banknote, a stamp, a security document, an identity card, a passport, a driver's license, a credit card, an access card, a ticket such as, e.g., a transportation ticket or an event ticket, a voucher, a value document, an ink-transfer film, a reflective film, a thread, a commercial good, and a cigarette packaging carrying or not carrying coded or encrypted information.

The present invention also provides a polymer wherein at least about 0.1% of the polymer molecules have bonded thereto 1 to 4 residues (e.g., 1, 2 or 3 residues) of formula -Q-(Y)$_w$ wherein Q represents an A or B or (A') or (B') moiety;
Y is selected from (i) halogen (e.g., F, Cl, Br and I),
(ii) optionally substituted N-heterocycloaliphatic groups having from 3 to about 8 ring members, at least one of which is N, which are bonded to Q through an N atom, and (iii) optionally substituted phenoxy groups bonded to Q through the O atom;
w represents an integer of from 1 to 4; and further provided that Q may at the same time be bonded to up to 4 polymer molecules (e.g., to 1, 2, 3 or 4 different polymer molecules).

In one aspect of the polymer, the polymer may be a compound of general formula (2):

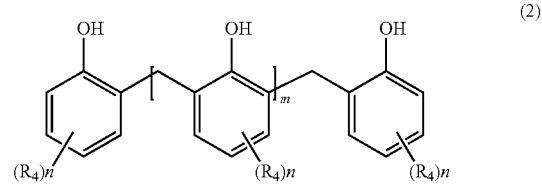

wherein the groups R$_4$, the same or different from each other, are selected from C$_1$-C$_{10}$ alkyl and C$_1$-C$_4$ alkoxy; m represents an integer of from 1 to about 30; and n represents an integer of from 1 to about 3.

Regarding x and w, examples of combinations thereof include wherein x is 1 and w=0; wherein x is 0 and w is 2 or not higher than 4; and wherein (x+w) is not higher than about 4.

In yet another aspect, the polymer may be obtainable by the process set forth above (including the various aspects thereof).

DETAILED DESCRIPTION OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description making apparent to those skilled in the art how the several forms of the present invention may be embodied in practice.

Regarding the meanings of the groups R, R', R", $R_1$, $R_2$, $R_3$ and $R_4$ mentioned herein, the following applies throughout the present specification and the appended claims (it being understood that throughout the present specification and the appended claims the indicated number of carbon atoms invariably refers to the respective unsubstituted group):

An "optionally substituted aliphatic" or "optionally substituted alkyl" group includes linear and branched alkyl groups which preferably have from 1 to about 12 carbon atoms, e.g., from 1 to about 8 carbon atoms, from 1 to about 6 carbon atoms, or from 1 to about 4 carbon atoms. Specific non-limiting examples thereof include methyl, ethyl, n-propyl, isopropyl, n-butyl, isobutyl, tert-butyl, sec-butyl, linear or branched pentyl (e.g., 2-methylbutyl, 2-ethylpropyl and 2,2-dimethylpropyl), linear or branched hexyl (e.g., 2-ethylbutyl, 3-ethylbutyl, 2,2-dimethylbutyl, 3,3-dimethylbutyl, and 2,3-dimethylbutyl), linear or branched heptyl, linear or branched octyl (e.g., 2-ethylhexyl), and linear or branched nonyl. The alkyl groups may be substituted with one or more substituents (e.g., one, two, three, four, etc.). Non-limiting examples of these substituents include OH, halogen such as, e.g., F, Cl, Br, and I (as in, e.g., trifluoromethyl, trichloromethyl, pentafluorethyl and 2,2,2-trifluoroethyl), alkoxy having from 1 to about 6 carbon atoms, e.g., from 1 to about 4 carbon atoms, such as, e.g., methoxy, ethoxy, propoxy and butoxy, acyloxy having from 1 to about 4 carbon atoms such as, e.g., acetoxy and propionyloxy, aryloxy having from about 6 to about 10 carbon atoms such as, e.g., (optionally substituted) phenoxy, aroyloxy having from about 6 to about 10 carbon atoms such as, e.g., benzoyloxy, —COOH (including partially or completely salified forms thereof), alkoxycarbonyl having from 1 to about 4 carbon atoms in the alkyl groups such as, e.g., methoxycarbonyl and ethoxycarbonyl, —$SO_3H$, alkylsulfonyl, arylsulfonyl, alkylsulfonylamino, nitro, cyano, amino, monoalkylamino and dialkylamino wherein the alkyl groups have from 1 to about 6 carbon atoms, e.g., from 1 to about 4 carbon atoms, such as, e.g., methylamino, dimethylamino, ethylamino, diethylamino, propylamino and dipropylamino. The alkyl groups may also be substituted by one or more optionally substituted cycloalkyl groups (preferably having from 3 to about 8 ring carbon atoms) as further set forth below. Preferred substituents for the alkyl groups include F, Cl, Br, OH, methoxy, ethoxy, —COOH, —$SO_3H$, amino, methylamino, ethylamino, dimethylamino and diethylamino. If more than one substituent is present, the substituents may be the same or different. Also, one or more (e.g., one or two) of the C atoms of the alkyl group may be replaced by a heteroatom such as, e.g., O, S and NR''' (with R''' representing, for example, H or alkyl having from 1 to about 4 carbon atoms). Further, the alkyl group may have one or more carbonyl groups (C=O) incorporated therein and/or may comprise one or more carbon-carbon double and/or triple bonds (such as in, e.g., vinyl, allyl and propargyl).

An "optionally substituted cycloaliphatic" or "optionally substituted cycloalkyl" group preferably comprises from about 3 to about 12 ring carbon atoms, more preferably from about 5 to about 8 ring carbon atoms such as, e.g., cyclopropyl, cyclobutyl, cyclopentyl, cyclohexyl, cycloheptyl and cyclooctyl. The cycloalkyl groups may be substituted with one or more substituents (e.g., one, two, three, four, etc). Non-limiting examples of these substituents include OH, halogen such as, e.g., F, Cl, Br, and I, alkoxy having from 1 to about 6 carbon atoms, e.g., from 1 to about 4 carbon atoms, such as, e.g., methoxy, ethoxy, propoxy and butoxy, acyloxy having from 1 to about 4 carbon atoms such as, e.g., acetoxy and propionyloxy, aryloxy having from about 6 to about 10 carbon atoms such as, e.g., (optionally substituted) phenoxy, aroyloxy having from about 6 to about 10 carbon atoms such as, e.g., benzoyloxy, —COOH (including partially or completely salified forms thereof), alkoxycarbonyl having from 1 to about 4 carbon atoms in the alkyl groups such as, e.g., methoxycarbonyl and ethoxycarbonyl, —$SO_3H$, alkylsulfonyl, arylsulfonyl, alkylsulfonylamino, nitro, cyano, amino, monoalkylamino and dialkylamino wherein the alkyl groups have from 1 to about 6 carbon atoms, e.g., from 1 to about 4 carbon atoms, such as, e.g., methylamino, dimethylamino, ethylamino, diethylamino, propylamino and dipropylamino. The cycloalkyl groups may also be substituted by one or more optionally substituted alkyl groups (preferably having from 1 to about 4 carbon atoms) as set forth above. Preferred substituents for the alkyl groups include F, Cl, Br, OH, methoxy, ethoxy, —COOH, —$SO_3H$, amino, methylamino, ethylamino, dimethylamino and diethylamino. If more than one substituent is present, the substituents may be the same or different. Further, the cycloalkyl group may have one or more carbonyl groups (C=O) incorporated therein and/or may comprise one or more carbon-carbon double bonds (such as in, e.g., cyclopentenyl and cyclohexenyl).

An "optionally substituted aryl (aromatic)" group and an "optionally substituted heteroaryl (heteroaromatic" group denote optionally fused aryl and heteroaryl groups which preferably comprise from about 5 to about 15 ring members, e.g., from about 6 to about 10 ring members. The heteroaryl groups will usually comprise from 1 to about 3 ring members selected from O, S and N and may be partially or fully hydrogenated. Specific examples of these aryl and heteroaryl groups include phenyl, naphthyl, anthranyl, phenanthryl, 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, indazolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3,4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, 1,3-benzodioxol-5-yl, 1,4-benzo-dioxane-6-yl, 2,1,3-benzothiadiazol-4- or -5-yl or 2,1,3-benzoxadiazol-5-yl, 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, 4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxaneyl, 1,3-dioxane-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or -6-yl, 2,3-(2-oxomethylenedioxy)phenyl, 3,4-dihydro-2H-1,5-benzodioxepin-6- or -7-yl, 2,3-dihydrobenzofuranyl, 2,3-dihydro-2-oxofuranyl. The aryl and heteroaryl groups may be substituted with one or more (e.g., one, two, three, four, etc.) substituents which are preferably selected from halogen such as, e.g., F, Cl, Br, and I, OH, —COOH (including partially or completely salified forms thereof), —SO$_3$H, nitro, cyano, alkoxy having from 1 to about 4 carbon atoms such as, e.g., methoxy and ethoxy, acyloxy having from 1 to about 4 carbon atoms such as, e.g., acetoxy and propionyloxy, aryloxy having from about 6 to about 10 carbon atoms such as, e.g., phenoxy, aroyloxy having from about 6 to about 10 carbon atoms such as, e.g., benzoyloxy, amino, monoalkylamino and dialkylamino wherein the alkyl groups have from 1 to about 6 carbon atoms, e.g., from 1 to about 4 carbon atoms, such as, e.g., methylamino, dimethylamino, ethylamino, diethylamino, propylamino and dipropylamino, acylamino having from 1 to about 8 carbon atoms such as, e.g., acetylamino and propionylamino, aminocarbonyl, monoalkylaminocarbonyl, diaminocarbonyl and alkoxycarbonyl having from 1 to about 4 carbon atoms in the alkyl groups such as, e.g., methoxycarbonyl and ethoxycarbonyl, optionally substituted acyl having from 2 to about 8 carbon atoms such as acetyl and propionyl, alkylsulfonyl, arylsulfonyl and alkylsulfonylamino. If more than one substituent is present, the substituents may be the same or different. Also, the aryl and heteroaryl groups may be substituted by aryl groups and/or alkylaryl groups. Specific and non-limiting examples of substituted aryl groups include chlorophenyl, dichlorophenyl, fluorophenyl, bromophenyl, phenoxyphenyl, hydroxyphenyl, dihydroxyphenyl, methoxyphenyl, aminophenyl, dimethylaminophenyl and biphenylyl.

An "optionally substituted alkylaryl" group and an "optionally substituted alkylheteroaryl" group denote optionally substituted aryl groups and optionally substituted heteroaryl groups as set forth above which are (further) substituted by at least one optionally substituted alkyl group (preferably comprising from 1 to about 6, e.g., from 1 to about 4 carbon atoms) as set forth above. Specific examples thereof include tolyl, xylyl, mesityl, ethylphenyl, cumyl, trifluormethylphenyl, hydroxytolyl, chlorotolyl, methylpyridyl, methylfuryl, methylthienyl, diisopropylphenyl, di(tert-butyl)phenyl, and methylnaphthyl.

An "optionally substituted arylalkyl" group and an "optionally substituted heteroarylalkyl" group denote optionally substituted alkyl groups (preferably comprising from 1 to about 6, e.g., from 1 to about 4 carbon atoms) as set forth above which are (further) substituted by at least one optionally substituted aryl group and/or optionally substituted heteroaryl group as further set forth above. Specific examples thereof include benzyl, methylbenzyl, chlorobenzyl, dichlorbenzyl, hydroxybenzyl, 1-phenylethyl, 2-phenylethyl, pyridylmethyl, thienylmethyl, furylmethyl, and naphthylmethyl.

An "optionally substituted and/or fused 5- to 7-membered ring" denotes a saturated, partially unsaturated or aromatic N-heterocyclic ring which in addition to the one or two N atoms already present therein may comprise one or two additional heteroatoms which are selected from O, N and S. The ring will usually have five or six ring members. Also, the ring will often comprise no additional heteroatom. Further, the ring may have one or two aromatic and/or heteroaromatic rings (e.g., benzene rings) fused to it and/or may be substituted with one or more (e.g., one, two, three, four, etc.) substituents which are preferably selected from F, Cl, Br, and I, OH, —COOH (including partially or completely salified forms thereof), —SO$_3$H, cyano, nitro, alkoxy having from 1 to about 4 carbon atoms such as, e.g., methoxy and ethoxy, acyloxy having from 1 to about 4 carbon atoms such as, e.g., acetoxy and propionyloxy, aryloxy having from about 6 to about 10 carbon atoms such as, e.g., phenoxy, aroyloxy having from about 6 to about 10 carbon atoms such as, e.g., benzoyloxy, amino, monoalkylamino and dialkylamino wherein the alkyl groups have from 1 to about 6 carbon atoms, e.g., from 1 to about 4 carbon atoms, such as, e.g., methylamino, dimethylamino, ethylamino, diethylamino, propylamino and dipropylamino, acylamino having from 1 to about 8 carbon atoms such as, e.g., acetylamino and propionylamino, aminocarbonyl, monoalkylaminocarbonyl, diaminocarbonyl and alkoxycarbonyl having from 1 to about 4 carbon atoms in the alkyl groups such as, e.g., methoxycarbonyl and ethoxycarbonyl, optionally substituted acyl having from 2 to about 8 carbon atoms such as acetyl and propionyl, alkylsulfonyl, arylsulfonyl and alkylsulfonylamino, optionally substituted alkyl having from 1 to about 6 carbon atoms such as, e.g., methyl, ethyl, hydroxymethyl and hydroxyethyl, optionally substituted (hetero)aryl such as, e.g., phenyl, tolyl, xylyl, hydroxyphenyl, pyridinyl and pyrrolyl, and optionally substituted alkylaryl such as, e.g., benzyl. If more than one substituent is present, the substituents may be the same or different. Non-limiting examples of unsubstituted N-containing 5- to 7-membered rings include pyrrolyl, pyrrolidinyl, pyridinyl, pyrimidinyl, piperidinyl, morpholinyl, piperazinyl, thienyl, pyrazolyl, pyrazolidinyl, oxazolyl and oxazolidinyl.

As set forth above, the compounds of the present invention include general formula (1):

$$(P—O)_x\text{-}Q\text{-}Y_w \tag{1}$$

wherein P represents a polymeric moiety having at least three repeating units which comprise an optionally substituted phenyl ring;
Q represents a polycyclic aromatic hydrocarbon moiety containing an S atom or S(═O)$_2$ moiety (i.e., a polycyclic aromatic hydrocarbon skeleton containing an S atom or S(═O)$_2$ moiety incorporated in its basic structure which may optionally comprise one or more substituents in addition to the substituents Y and/or P—O);
Y is selected from (i) halogen, (ii) optionally substituted N-heterocycloaliphatic groups having from 3 to about 8 ring members and which are bonded to Q through an N atom, and (iii) optionally substituted phenoxy groups;
x represents an integer of from 0 to 4;
w represents an integer of from 0 to 4
and wherein w and x are not simultaneously 0;
provided that when x=0 at least one Y is selected from (ii) and (iii).

If more than one halogen is present (i.e., if w is at least 3), the halogen atoms may be the same or different and are preferably the same. Further, if more than one optionally substituted N-heterocycloaliphatic group having from 3 to about 8 ring members is present, the groups may be the same or different as well (and preferably are the same). Further, if more than one optionally substituted phenoxy group is present, the groups may be the same or different as well (and preferably are the same). Further, x will often be 1 or 2, more preferably 1, and the sum (x+w) will often not exceed 6, e.g., not exceed 5, or not exceed 4.

It also is to be appreciated that while a group (P—O)— will usually be bonded directly to the moiety Q, it may also be bonded to an aromatic group (in particular, a phenyl group) which is not part of the Q skeleton but is (a part of) a substituent thereof. In this regard, the above formulae (II), (V), (D) and (G) may be referred to. In the case of compounds of formulae (II), (V), (D) and (G), the group (P—O)— is bonded to the optionally substituted phenyl ring of a group —CO—NR—CO— (which is one of the meanings of Z and X in formulae (A), (B), (E) and (H)) wherein R represents an optionally substituted phenyl group. It is also possible for bonding to —C(=NR')—NR—CO— wherein (P—O)— may be bonded to an aromatic group R and/or R').

Group Y can be selected from N-heterocycloaliphatic groups having from 3 to about 8 ring members (e.g., 3, 4, 5, 6, 7 or 8 ring members), which ring members may comprise from 1 to about 3 heteroatoms (e.g., 1, 2 or 3 heteratoms) selected from N, S, and O, provided that at least one ring member is N. At least one (and preferably at least two) of the ring members are carbon atoms. By way of non-limiting example, a heterocycloaliphatic group Y may have 5, 6 or 7 ring members (preferably 5 or 6 ring members) and contain 1 or 2 heteroatoms, at least one of them being an N atom. If two heteroatoms are present, the second heteroatom may be N, S or O. If three heteroatoms are present, the second or third heteroatom may be the same or different and be selected from N, O and S. For example, a heterocycloaliphatic group Y containing 3 heteroatom ring members may contain 3 N atoms, or 2 N atoms and one O atom or one S atom.

The heterocycloaliphatic groups Y may further be substituted by one or more substituents (e.g., 1, 2, 3 or 4 substituents and preferably not more than 3, or not more than 2 substituents) selected from alkyl and alkoxy groups comprising up to about 10 carbon atoms (e.g., 1, 2, 3, 4, 5 or 6 carbon atoms). Non-limiting examples of corresponding substituents include ethyl, methyl, n-propyl, i-propyl, n-butyl, sec.-butyl, and tert.-butyl and the corresponding alkoxy groups.

For example, group Y may be a group that is the residue of a compound (i.e., without H atom bonded to the nitrogen atom) selected from optionally substituted azacyclooctane, optionally substituted azepane, optionally substituted piperidine, optionally substituted piperazine, optionally substituted pyrrolidine, optionally substituted azetidine, optionally substituted aziridine, optionally substituted morpholine, optionally substituted oxazolidine, optionally substituted pyrazolidine, optionally substituted isopyrazolidine, optionally substituted isoxazolidine, and optionally substituted thiazolidine. The optional substituents on the heterocyclic rings (e.g., 1, 2, 3 or 4 substituents) may be the same or different and may preferably be selected from $C_1$-$C_4$ alkoxy and $C_1$-$C_6$ alkyl groups. A specific and non-limiting example of a correspondingly substituted group is 3,5-dimethyl-1-piperidinyl.

Group Y may be additionally selected from optionally substituted phenoxy group, wherein the phenoxy groups may be substituted by one or more (e.g., 1, 2 or 3 identical or different) substituents selected from halogen (e.g., F, Cl, Br and I), nitro, cyano, NRR', $SO_3H$ and COOH and salts and derivatives of these sulfonic and carboxylic acid groups (e.g., salts of alkali and alkaline earth metals such as Na, K, Ca, and Mg, esters such as $C_1$-$C_4$ alkyl esters, and amides such as amides with NRR' as amido moiety), OH, heterocycloalkyl comprising up to three heteroatoms selected from O, N and S as ring members and from 3 to about 8 ring members, and alkyl (including cycloalkyl) and alkoxy (including cycloalkoxy) groups comprising from 1 to about 10 carbon atoms (e.g., 1, 2, 3, 4, 5 or 6 carbon atoms). Specifics and non-limiting example of a correspondingly substituted phenoxy group are 2,6-di-tert-butyl-4-methylphenoxy, p-cresyl, and o-cresyl.

A polymeric moiety P in a polymer-bonded compound of general formula (1) preferably comprises only carbon atoms (i.e., no heteroatoms such as O, N or S) in the backbone thereof. Also, the polymeric moiety preferably comprises at least three aromatic rings (e.g., phenyl rings) in the backbone thereof. These aromatic rings (which may be the same or different and preferably are the same) may be connected to each other either directly or through one or more atoms, preferably carbon atoms. At least some (and preferably all) of these aromatic rings may carry one or more (e.g., 1, 2 or 3) polar (heteroatom containing) substituents that increase the solubility of the polymeric moiety in polar media (such as, e.g., alcohol, etc.) compared to the polymeric moiety without polar substituent(s). If more than one polar substituent is present, the substituents may be the same or different. Of course, one or more additional (non-polar) substituents may be present on an aromatic ring as well. By way of non-limiting example, the polymeric moiety may be derived from a phenolic resin such as, e.g., a novolac resin and in particular, a phenolic resin having at least about 3 hydroxy groups and/or a (weight) average molecular weight of at least about 300, e.g., at least about 350, and not higher than about 3,000, e.g., not higher than about 1,500. For example, P may be derived from (be the residue of) a compound of general formula (2):

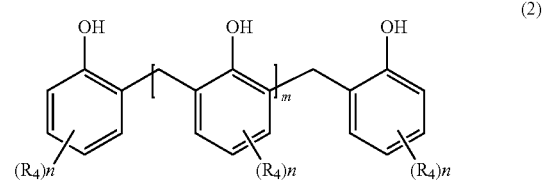

wherein the groups $R_4$, the same or different from each other, are selected from $C_1$-$C_{10}$ alkyl and $C_1$-$C_4$ alkoxy; m represents an integer of from 1 to about 30, e.g., from 1 to 25, from 1 to 15, from 1 to 10, from 1 to 5, from 1 to 3, from 5 to 15, from 5 to 10, from 10 to 20, or from 20 to 30; and n represents an integer of from 1 to 3 (e.g., 1, 2 or 3). For example, m may represent an integer of from 1 to 10 and/or n may be 1 or 2 and/or the groups $R_4$ may independently be selected from $C_1$-$C_{10}$ alkyl such as, e.g., isopropyl, tert-butyl, tert-octyl, n-nonyl and branched nonyl. Further, a group $R_4$ may be in the meta- or para-position with respect to the OH group. For example, if two groups $R_4$ are present on a phenyl ring (the same or different, preferably the same groups $R_4$) they may be present in any of the available positions on the phenyl ring, such as, e.g., meta/para or meta/meta with respect to the OH group.

One of skill in the art will appreciate that compounds of general formula (2) will often be present as a mixture of compounds with different values of m. In this case, the average value of m in the general formula (2) will often be at least about 1, e.g., at least about 2, e.g., at least about 3, or at least about 4, and will also often be not higher than about 30, e.g., not higher than about 20, not higher than about 15, or not higher than about 10.

As also set forth above, Q may be a moiety having a basic structure of formula (A) or (B) or (A') or (B'):

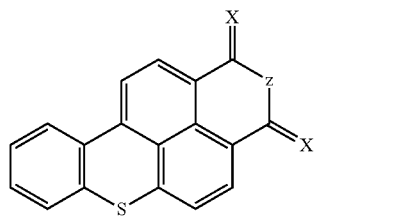
(A)

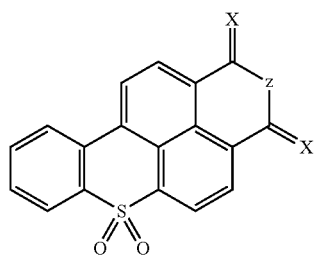
(A')

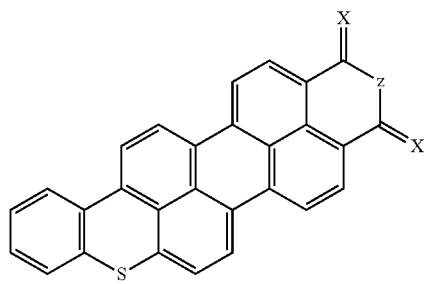
(B)

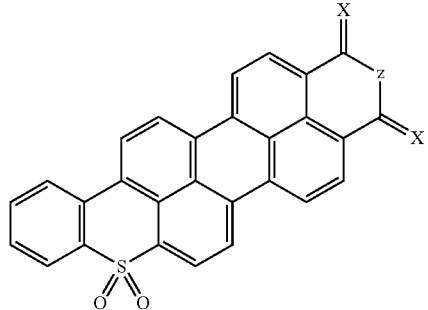
(B')

In the above formulae (A) and (B) or (A') or (B'), Z represents O, S or N—R, and X, which can be the same or different, represents O, S, or NR'. Thus, the group formed by Z and X can be represented, for example, by —CO—Z—CO— (may be replaced by [—COOH HOOC—] (i.e., the dicarboxylic acid instead of the anhydride)), —CS—Z—CO—, —CS—Z—CS—, or —C(=NR')—NR—CO—.

The groups R and R' in the above formulae independently represent an optionally substituted aliphatic, cycloaliphatic, aromatic, heteroaromatic, alkylaryl, alkylheteroaryl, arylalkyl or heteroarylalkyl group having from 1 to about 20 carbon atoms. Additionally, R and R' may be combined to form, together with the N atoms to which they are attached, an optionally substituted and/or fused 5- to 7-membered ring.

There are also provided optionally substituted compounds of formula (B) or (B')

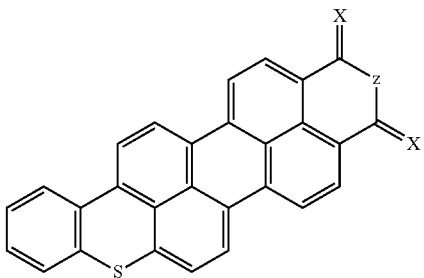
(B)

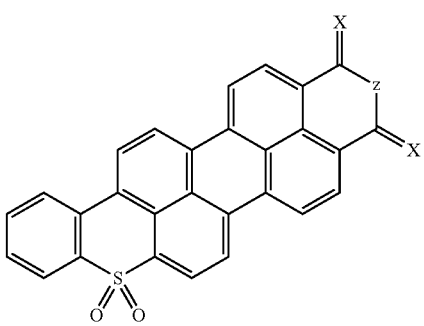
(B')

wherein Z represents O, S or N—R, and X, which can be the same or different, represents O, S, or NR'. Thus, the group formed by Z and X can be represented, for example, by —CO—Z—CO— (may be replaced by [—COOH HOOC—] (i.e., the dicarboxylic acid instead of the anhydride)), —CS—Z—CO—, —CS—Z—CS—, or —C(=NR')—NR—CO—; and R and R' independently represent an optionally substituted aliphatic, cycloaliphatic, aromatic, heteroaromatic, alkylaryl, alkylheteroaryl, arylalkyl or heteroarylalkyl group having from 1 to about 20 carbon atoms; and R and R' may also be combined to form, together with the N atoms to which they are attached, an optionally substituted and/or fused 5- to 7-membered ring.

These compounds can include compounds of formulae (C), (D) or (E) or (F) or (G) or (H):

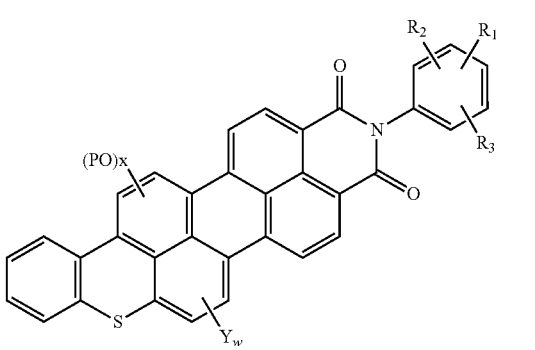
(C)

-continued (D)
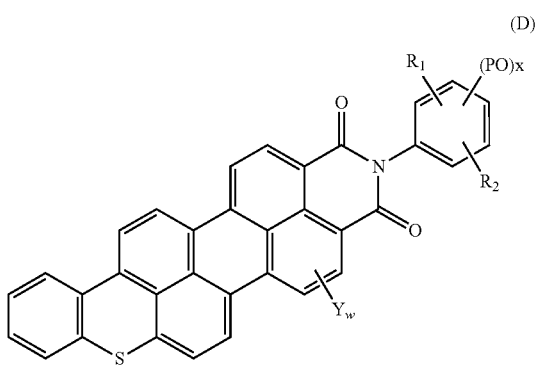

(E)
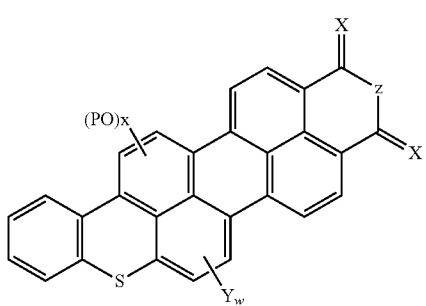

(F)
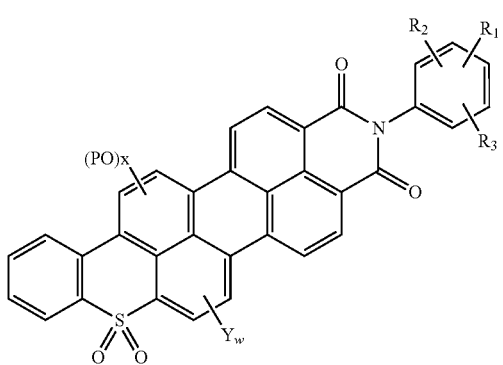

(G)
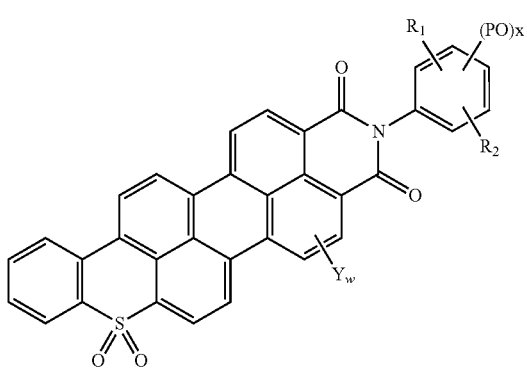

-continued (H)
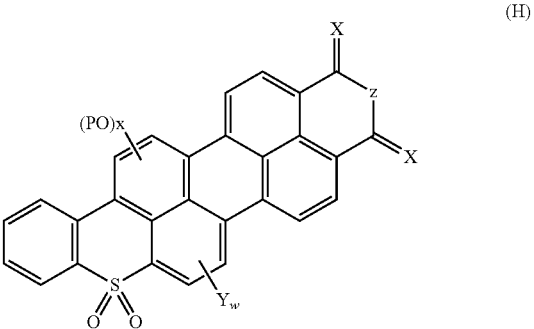

wherein in the case of formula (E) and (H), Z represents O, S or N—R; and X, which can be the same or different, represents O, S, or NR'; and R and R' independently represent an optionally substituted aliphatic, cycloaliphatic, aromatic, heteroaromatic, alkylaryl, alkylheteroaryl, arylalkyl or heteroarylalkyl group having from 1 to about 20 carbon atoms; and R and R' may be combined to form, together with the N atoms to which they are attached, an optionally substituted and/or fused 5- to 7-membered ring;

$R_1$, $R_2$ and $R_3$ are independently selected from hydrogen, $C_1$-$C_4$ alkyl, $C_1$-$C_4$ alkyl-COOH, $C_1$-$C_4$ alkyl-$SO_3H$, $C_1$-$C_4$ alkoxy, mono($C_1$-$C_4$)alkylamino, di($C_1$-$C_4$)alkylamino, $C_1$-$C_4$ aminoalkyl, halogen, cyano, nitro, and $SO_3H$, the alkyl groups being optionally substituted;

Y is selected from (i) halogen and (ii) optionally substituted N-heterocycloaliphatic groups having from 3 to about 8 ring members and which are bonded to an aromatic ring through an N atom; and (iii) optionally substituted phenoxy groups which are bonded to an aromatic ring through an O atom, the phenoxy group may be substituted by one or more substituents selected from halogen, nitro, cyano, NRR', $SO_3H$ and COOH and salts and derivatives of these sulfonic and carboxylic acid groups, OH, heterocycloalkyl comprising up to three heteroatoms selected from O, N and S as ring members and from 3 to about 8 ring members, and alkyl (including cycloalkyl) and alkoxy (including cycloalkoxy) groups comprising from 1 to about 10 carbon atoms;

P represents a polymeric moiety having at least three repeating units which comprise an optionally substituted phenyl ring;

and x is an integer of from 0 to 4; and w is an integer of from 0 to 4.

The compounds formula (B) or (B') can be unsubstituted.

Compounds of general formula (1) may be made, for example, by a process which comprises reacting in an aprotic polar organic solvent a compound of formula Q-(Hal)$_v$, wherein Hal represents halogen (e.g., F, Cl, Br or I) and v represents an integer of from 1 to 8 (e.g., 1, 2, 3, 4, or 5), with a compound selected from (a) N-containing cycloaliphatic compounds, (b) polymeric compounds of formula P—OH, and (c) optionally substituted phenolic compounds or by reacting a compound of formula Q-(Hal)$_v$ successively with two (if v is at least 2) or three (if v is at least 3) or even more compounds which are independently selected from compounds (a), (b) and (c). In the latter case the at least two compounds which are reacted successively with a compound of formula Q-(Hal)$_v$ may belong to the same group or a different group. For example, the compound of formula Q-(Hal)$_v$ may successively be reacted with two different compounds (a) or a compound (a) and a compound (b) in any order. Usually at least the reaction involving the N-containing cycloaliphatic compound (and usually also the reaction involving the reaction comprising the polymeric compound and/or the phenolic compound) may be carried out in the presence of an inorganic base and/or a strong organic non-nucleophilic base. The polar solvent usually comprises at least one solvent in which the polymeric compound, if used, is soluble and/or is at least one of N-methylpyrrolidone, dimethyl formamide, dimethyl acetamide, and dimethylsulfoxide.

A corresponding process may, for example, be represented by the following reaction schemes (1) or (2) or (3) or (4):

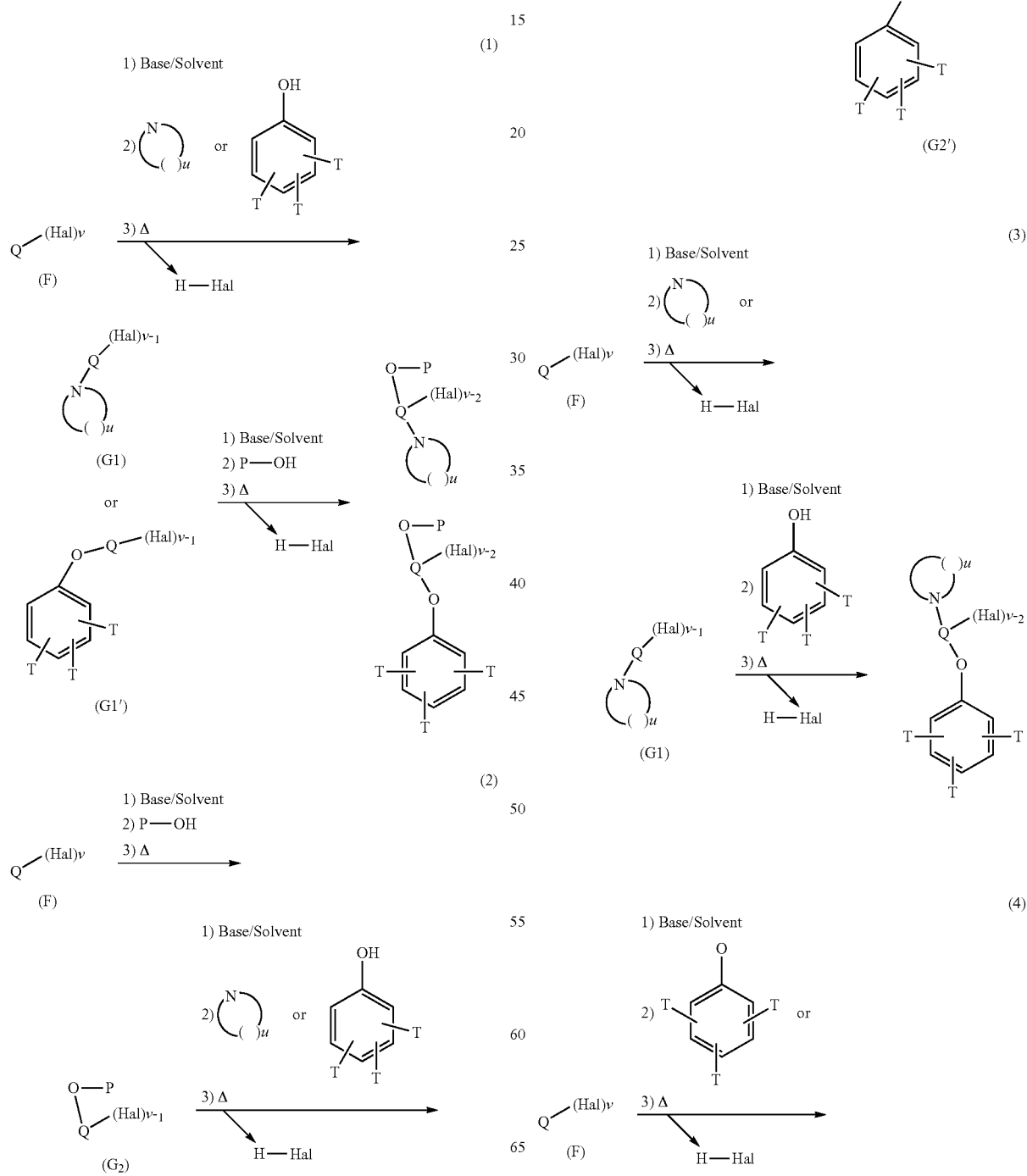

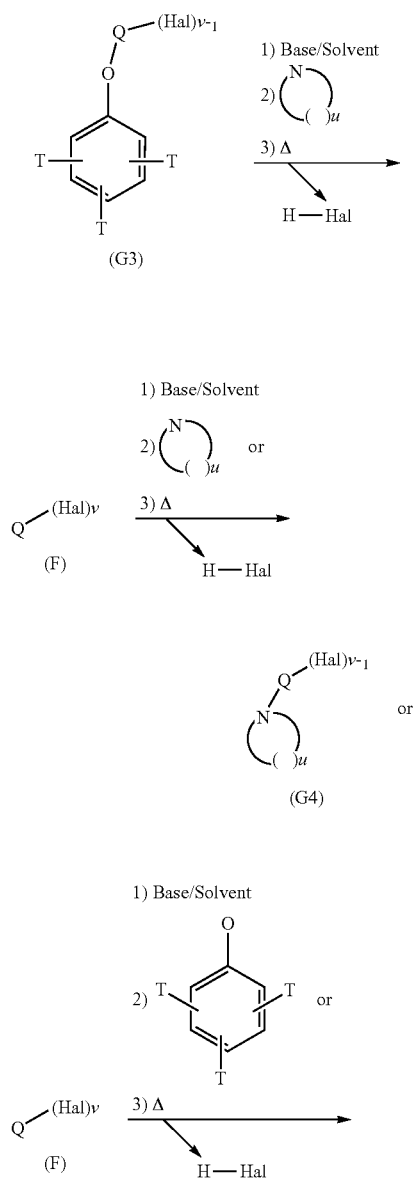

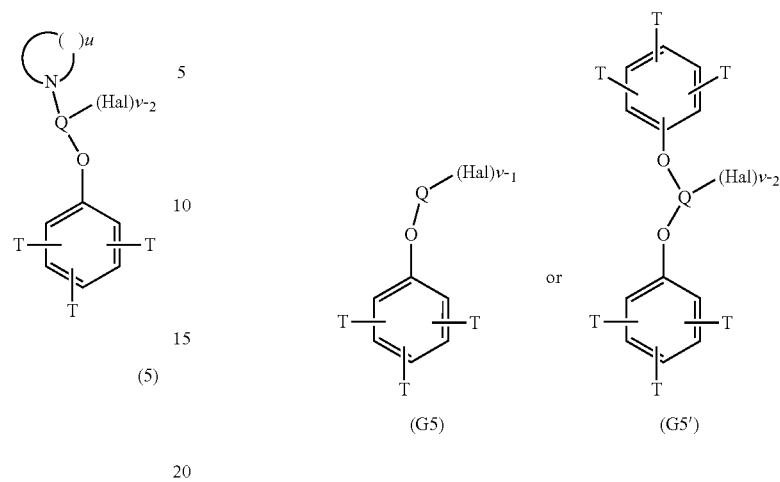

wherein P and Q are defined as above;
wherein T is selected from, but not limited to, halogen (e.g., F, Cl, Br and I), nitro, cyano, NRR', $SO_3H$ and COOH and salts and derivatives of these sulfonic and carboxylic acid groups (e.g., salts of alkali and alkaline earth metals such as Na, K, Ca, and Mg, esters such as $C_1$-$C_4$ alkyl esters, and amides such as amides with NRR' as amido moiety), OH, heterocycloalkyl comprising up to three heteroatoms selected from O, N and S as ring members and from 3 to about 8 ring members, and alkyl (including cycloalkyl) and alkoxy (including cycloalkoxy) groups comprising from 1 to about 10 carbon atoms (e.g., 1, 2, 3, 4, 5 or 6 carbon atoms);

Hal represents halogen;
( ) represents $CH_2$ wherein at least one $CH_2$ group can be replaced by O, NH or S;
u is from 2 to 7;
v is an integer of from 2 to 8;
and the symbol "Δ" represents the application of heat (heating).

F is the halogenated compound having a Q core as defined above. G1 or G2 or (G3) are the intermediates of reaction, when running the processes (1) or (2) or (3) or (4).

In the case of when running the process (5) and (6) which lead to compounds (G4) or (G5) or (G4') or (G5') v is an integer from 1 to 8.

Other alternatives processes are also possible to obtain the compounds according to formula (1) such as processes (7) or (8):

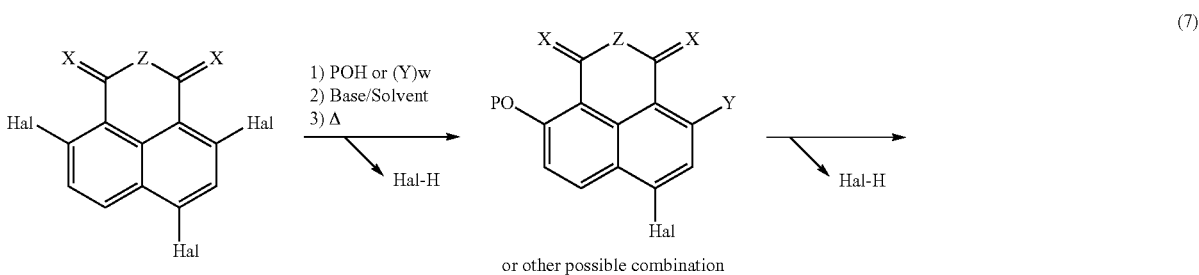

(7)

or other possible combination

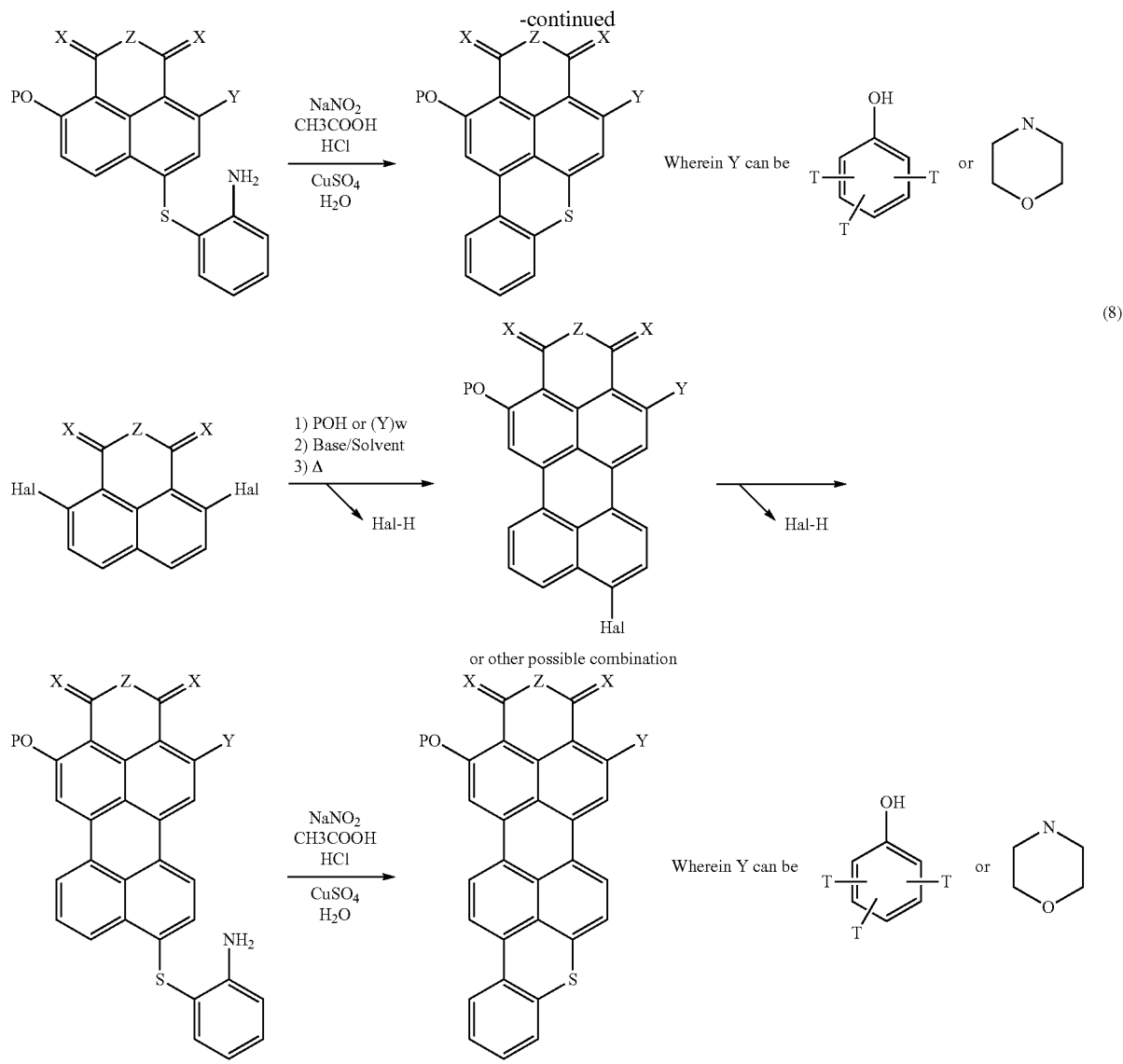

(8)

wherein the definitions of T, Hal, X, Z, POH, Y and w are the same as above defined.

It is to be appreciated that while the above reaction schemes show reactions wherein the compound obtained after the first step is reacted with one or more additional compounds these reaction schemes also illustrate processes for making compounds of the present invention such as those of formula (1) wherein only one halogen atom of a compound of formula Q-(Hal)$_v$ is replaced by a compound selected from N-containing cycloaliphatic compounds, polymeric compounds of formula P—OH, and optionally substituted phenolic compounds, i.e., wherein the process is complete after the first step (i.e., no further reactions will take place).

If one of the above processes is to be selected, it will usually be preferred to employ the process that will afford the intermediate (after the first step) that exhibits the higher solubility.

Examples of inorganic and organic bases suitable for catalyzing nucleophilic substitution reactions are well known to those of skill in the art. An example of a suitable inorganic base is $K_2CO_3$. Reaction temperatures will often range from about 50° C. to about 140° C., also depending on the boiling point of the solvent used. It further will often be desirable to employ an anti-foam agent such as, e.g., a polyethylene glycol or derivative thereof. The reaction product (e.g., polymer-bonded compound of formula (1)) can usually be isolated from the resultant reaction mixture and optionally purified by conventional means such as, e.g., filtration, centrifugation, extraction, chromatographic methods, etc.

The weight ratio of compound(s) of formula Q-(Hal)$_v$ (or similar compounds) to polymeric compound(s) of formula P—OH (or a similar polymeric compounds) depends on several factors such as, e.g., the molecular weight(s) of compound(s) of formula Q-(Hal)$_v$, the average number of compound(s) of formula Q-(Hal)$_v$ that is/are to be bonded to a single polymer molecule or the average number of polymer molecules that are to be bonded to a single compound of formula Q-(Hal)$_v$ (or a similar compound). In particular, in a polymer-bonded compound of the present invention a single polymer molecule P may have one or more than one unit Q (e.g., an average of 1, 2, 3, 4 of units Q) bonded thereto. Conversely, one or more than one polymer molecule (e.g., an average of 1, 2, 3, 4, or more polymer molecules) may be bonded to a single unit Q. It also is to be appreciated that it is possible to employ as starting materials and intermediates in the reactions represented by the above reaction schemes not only individual compounds but also mixtures of compounds with different values of v (and even different values of u). For example, a starting material of formula Q-(Hal)$_v$ may be a mixture of two compounds (not taking into account positional isomers) wherein v represents 5 or 6. Likewise, even if a single compound of formula Q-(Hal)$_v$ also named (G) is employed as starting material, depending on the reaction conditions the intermediate obtained after the first reaction may be a single compound or a mixture of compounds such as, e.g., a mixture of three compounds (not taking into account positional isomers) wherein, for example, 1, 2 or 3 halogen atoms are replaced by a group P—O— or an N—heterocycloaliphatic ring.

It further is possible (and sometimes preferred) to employ a relatively large stoichiometric excess of polymer(s) with respect to compound(s) of formula Q-(Hal)$_v$ (or similar compounds). This will result in a polymer wherein only a small fraction (e.g., not more than about 0.1%, not more than about 0.5%, not more than about 1%, or not more than about 2%, not more than about 4%, not more than about 6%, not more than about 8%, not more than about 10%) of the polymer molecules have at least one unit Q bonded thereto, thereby affording a doped polymer of the present invention. The doped polymer can be used for the same purposes for which the polymer-bonded compound of the present invention is employable such as, e.g., as a component of a printing ink composition.

It is, of course, possible to react one compound of formula Q-(Hal)$_v$ (or a similar compound) with more than one (or more than one type of) polymer. By way of non-limiting example, a compound of formula Q-(Hal)$_v$ (or a similar compound) may be reacted with a mixture of polymers of the above formula (2). Conversely, two or more different compounds of formula Q-(Hal)$_v$ (e.g., two or more compounds with different values for v and/or different meanings of Hal) may be reacted with (bonded to) a single (type of) polymer. Finally, two or more different compounds of formula Q-(Hal)$_v$ (or similar compounds) may be reacted with two or more different (types of) polymers, although this will usually result in difficult to control product mixtures.

A printing ink composition in accordance with the present invention comprises a (preferably polar) liquid medium and one or more (types of) compounds of general formula (1) and/or compounds of the other formulas as set forth above (e.g., a mixture of one, two or three different compounds of general formula (1)) or any of the other formulas) dissolved or dispersed in the medium. The concentration of the compound(s) of general formula (1) and/or compounds of the other formulas in the medium depends on several factors such as, e.g., the polymer(s) to which the Q-containing compounds is/are bonded, the desired color intensity, the liquid medium, the remaining (optional) components of the composition, the intended purpose of the printing ink composition, and the substrate onto which the printing ink composition is to be applied. Often the (total) concentration of the one or more compound(s) of general formula (1) and/or compounds of the other formulas in the printing ink composition will be at least about 0.01%, at least about 0.02%, or at least about 0.05% by weight, and will usually be not higher than about 40% by weight, e.g. not higher than about 20%, not higher than about 10%, or not higher than about 5% by weight based on the total weight of the composition. The use of a mixture of different compounds permits for complex marking to provide an advantageous composition to render documents difficult to forge. Thus, for example, a mixture of different compounds in a printing ink composition permits the making of unique "chemical keys" that can be fine tuned by varying the concentrations and/or the compounds included in the composition.

The intended purpose of the printing ink composition is one of several factors which determines suitable and desirable concentration ranges for the compounds of general formula (1) and/or compounds of the other formulas as well as the types and concentration ranges of suitable or desirable optional components of the composition. There are many different types of printing processes. Non-limiting examples thereof include inkjet printing (thermal, piezoelectric, continuous, etc.), flexography, intaglio printing (e.g., gravure printing), screen printing, letterpress printing, offset printing, pad printing, relief printing, planographic printing and rotogravure printing. In a preferred embodiment, a printing ink composition in accordance with the present invention is suitable (at least) for inkjet printing. Industrial inkjet printers, commonly used for numbering, coding and marking applications on conditioning lines and printing presses, are particularly suitable. Preferred ink-jet printers include single nozzle continuous ink-jet printers (also called raster or multi level deflected printers) and drop-on-demand ink-jet printers, in particular valve jet printers. Accordingly, the following discussion of printing ink compositions relates primarily to compositions for inkjet printing. However, it is to be kept in mind that the present invention is not limited to printing ink compositions for inkjet printing but rather encompasses all printing ink compositions in which compounds of the present invention can be employed. Accordingly, the following considerations and statements apply mutatis mutandis to all printing ink compositions in which the compounds in accordance with the teaching of the present invention are useful.

Printing inks in general comprise coloring agents and liquid vehicles which comprise solutions of resinous binders in solvents. The specific choice of binders and solvents depends on several factors, such as, for example, the compound(s), the remaining components that are to be present, and the nature of the substrate to be printed. Non-limiting examples of suitable binders for use in the ink compositions for inkjet printing include binders which are conventionally used in inkjet printing inks, including resins such as nitrocellulose, acrylate resins and polyester resins (such as, e.g., DYNAPOL® L 1203, L 205, L 206, L 208, L 210, L 411, L 651, L658, L 850, L 912, L 952, LH 530, LH 538, LH 727, LH 744, LH 773, LH 775, LH 818, LH 820, LH 822, LH 912, LH 952, LH 530, LH 538, LH 727, LH 744, LH 773, LH 775, LH 818, LH 820, LH 822, LH 823, LH 826, LH 828, LH 830, LH 831, LH 832, LH 833, LH 838, LH898, LH 908, LS436, LS615, P1500, S1218, S1227, S1247, S1249, S1252, S1272, S1401, S1402, S1426, S1450, S1510, S1606, S1611, S243, S320, S341, S361, S394, and S EP1408 from Evonik). Of course, other suitable resins known to those of skill in the art may be used as well. A typical (total) concentration of the one or more binders in the printing ink composition is from about 0.5% to about 10% by weight, based on the total weight of the composition. In this regard, it further is to be taken into account that typical viscosity values for inkjet printing inks are in the range of from about 4 to about 30 mPa·s at 25° C.

It further is to be appreciated that the polymer which has one or more units Q bonded thereto (and in the case of the doped polymer of the present invention as set forth above, also the polymer which is not bonded to any Q-containing molecule but is present in admixture with polymer that has a Q-containing unit bonded thereto) may also act as a binder for the composition. At any rate, the (principal) binder of the ink composition must be compatible with the polymer which a Q-containing unit bonded thereto, e.g., must not result in the formation of any insoluble substance, etc. when combined with the later.

Suitable solvents for inkjet printing inks are known to those of skill in the art. Non-limiting examples thereof include low-viscosity, slightly polar and aprotic organic solvents, such as, e.g., methyl ethyl ketone (MEK), acetone, ethyl acetate, ethyl 3-ethoxypropionate, toluene and mixtures of two or more thereof.

In particular if the printing ink composition of the present invention is to be applied by continuous inkjet printing the composition will usually also comprise at least one conductivity imparting agent (for example, a salt). The conductivity imparting agent will have a non-negligible solubility in the composition. Non-limiting examples of suitable conductivity imparting agents include salts such as, e.g., tetraalkyl ammonium salts (e.g., tetrabutyl ammonium nitrate, tetrabutyl ammonium perchlorate and tetrabutyl ammonium hexafluorophosphate), alkali metal thiocyanates such as potassium thiocyanate, akali potassium salts such as $KPF_6$ and alkali metal perchlorates such as lithium perchlorate. The conductivity imparting agent will be present in a concentration which is sufficient to provide the conductivity which is required or desirable. Of course, mixtures of two or more different conductivity imparting agents (salts) can be used. Often the one or more conductivity imparting agents will be present in a total concentration of from about 0.1% to 2% by weight, based on the total weight of the composition.

The printing ink composition according to the present invention may furthermore comprise one or more customary additives, such as, for example, fungicides, biocides, surfactants, sequestering agents, pH adjusters, etc. in the amounts customary for these additives. Further, the printing ink composition may comprise one or more additional colorants and/or components which impart a specific optical property (i.e., components which are different from the polymer-bonded compounds of the present invention). These additional components may be selected from, for example, conventional pigments and dyes, luminescent (e.g., fluorescent) pigments and dyes, and cholesteric and/or nematic liquid crystals. Examples of luminescent pigments include certain classes of inorganic compounds such as the sulphides, oxysulphides, phosphates, vanadates, garnets, spinels, etc. of non luminescent cations, which are doped with at least one luminescent transition-metal or a rare-earth metal cation. In order to strengthen the security of the ink composition may further comprise one or more pigments and/or dyes which absorb in the visible or invisible region of the electromagnetic spectrum and/or may further comprise one or more pigments and/or dyes which are luminescent. Non-limiting examples of suitable pigments and/or dyes which absorb in the visible or invisible region of the electromagnetic spectrum include phthalocyanine derivatives. Non-limiting examples of suitable luminescent pigments and/or dyes include lanthanide derivatives. The presence of pigment(s) and/or dye(s) will enhance and reinforce the security of the marking against counterfeiting.

The substrate or article which is to be provided with a marking and/or security feature in accordance with the present invention is not particularly limited and can be of various types. The substrate or article may, for example, consist (essentially) of or comprise one or more of a metal (for example, in the form of a container such as a can for holding various items such as, e.g., beverages or foodstuffs), optical fibers, a woven, a coating, and equivalents thereof, a plastic material, a ceramic material, glass (for example, in the form of a capsule or container such as a bottle for holding various items such as, e.g., beverages or foodstuffs), cardboard, packaging, paper, and a polymeric material. It is pointed out that these substrate materials are given exclusively for exemplifying purposes, without restricting the scope of the invention.

The substrate may furthermore already carry at least one marking or security element which comprises a substance selected from, e.g., inorganic luminescent compounds, organic luminescent compounds, IR-absorbers, magnetic materials, forensic markers, and combinations thereof. The marking or security element can be present in the form of indicia or a data matrix. on the substrate surface or be incorporated (embedded) in the substrate itself. The marking can be present also in the form of a cloud of dots or a specific pattern visible and/or invisible to the naked eye, randomly or not distributed in the item or article or goods or security documents or what is described above to be intended to be protected and/or authenticated.

The present invention will be more specifically explained with reference to examples. However, the scope of the present invention is not limited to the following examples.

EXAMPLES

Preparation of 4,4',4"-((2-(2,6-diisopropylphenyl)-1, 3-dioxo-2,3-dihydro-1H-thioxantheno[2,1,9-def] isoquinoline-4,8,12-triyl)tris(oxy))tribenzenesulfonate. The orange solid of sodium 4,4',4"-((2-(2, 6-diisopropylphenyl)-1,3-dioxo-2,3-dihydro-1H-thioxantheno[2,1,9-def]isoquinoline-4,8,12-triyl)tris(oxy))tribenzenesulfonate Compound 4,8,12-trichloro-2-(2,6-diisopropylphenyl)-1H-thioxantheno[2,1,9-def]isoquinoline-1,3(2H)-dione (0.3 g), sodium 4-hydroxybenzenesulfonate (0.41 g) and anhydrous potassium carbonate (0.73 g) were added to 10 mL of N-methyl-2-pyrrolidinone (NMP). The solution was heated at 130° C. with good stirring within 4 hours. After boiling a further 4 hours, the solution was cooled at room temperature, after a minute the liquor was added to dichloromethane (100 ml) and the precipitate was filtered and dried at 60° C. to give a orange solid of sodium 4,4',4"-((2-(2,6-diisopropylphenyl)-1,3-dioxo-2,3-dihydro-1H-thioxantheno[2,1,9-def]isoquinoline-4,8,12-triyl)tris(oxy))tribenzenesulfonate. The orange solid of sodium 4,4',4"-((2-(2,6-diisopropylphenyl)-1,3-dioxo-2,3-dihydro-1H-thioxantheno[2,1,9-def]isoquinoline-4,8,12-triyl)tris(oxy))tribenzenesulfonate (0.1 g) was given with a nominal yield of 18.0%. MS: base peak 1046

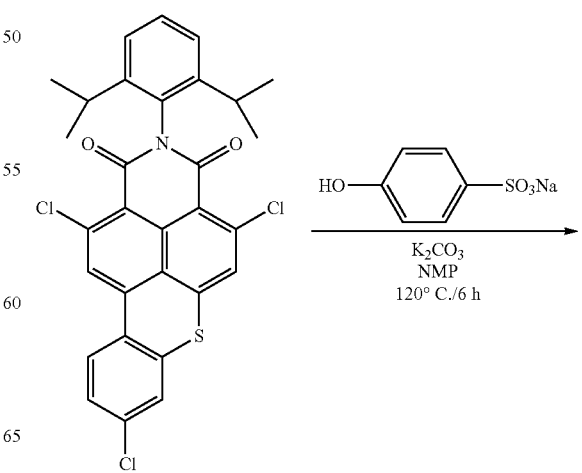

33

-continued

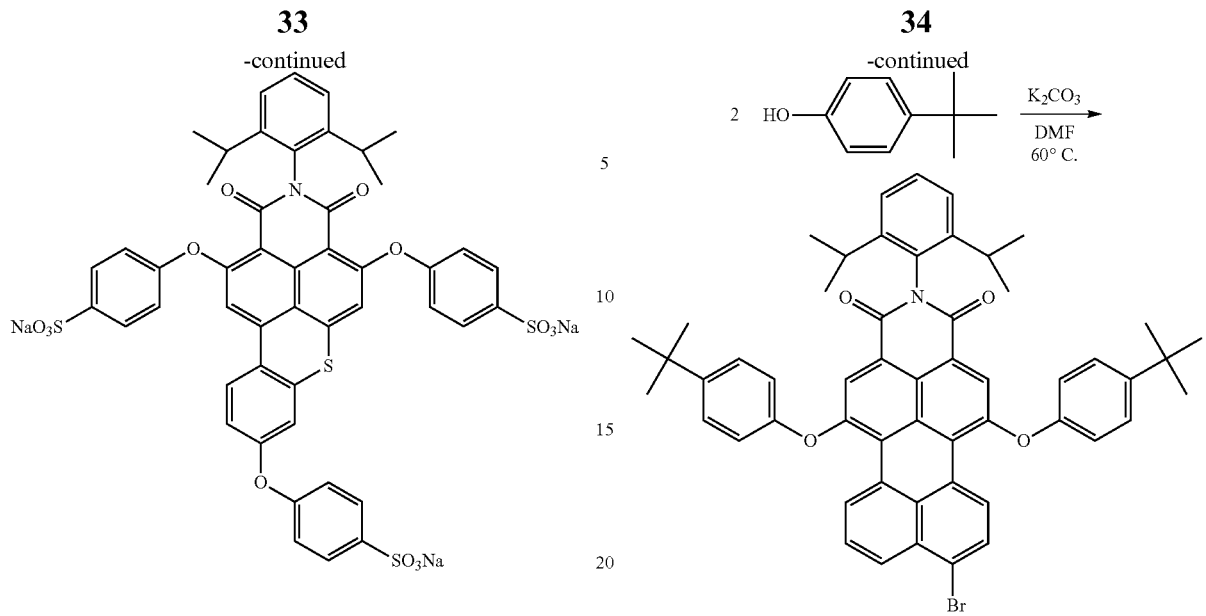

Preparation of 8-bromo-5,12-bis(4-(tert-butyl)phenoxy)-2-(2,6-diisopropylphenyl)-1H-benzo[5,10]anthra[2,1,9-def]isoquinoline-1,3(2H)-dione Compound 8,5,8,12-tribromo-2-(2,6-diisopropylphenyl)-1H-benzo[5,10]anthra[2,1,9-def]isoquinoline-1,3(2H)-dione (5.0 g), 4-(tert-butyl)phenol (2.09 g) and anhydrous potassium carbonate (2.18 g) were added to 166 mL of N,N-dimethylformamide (DMF). The solution was heated at 60° C. with good stirring within 4 hours. After boiling a further 4 hours, the solution was cooled at room temperature, after a minute the liquor was added to 30% aqueous hydrochloride acid (600 ml) filtered and dried at 60° C. to give a red solid of 8-bromo-5,12-bis(4-(tert-butyl)phenoxy)-2-(2,6-diisopropylphenyl)-1H-benzo[5,10]anthra[2,1,9-def]isoquinoline-1,3(2H)-dione The solid was purified on Chromatography Column to eliminate by-products. The red solid of 8-bromo-5,12-bis(4-(tert-butyl)phenoxy)-2-(2,6-diisopropylphenyl)-1H-benzo[5,10]anthra[2,1,9-def]isoquinoline-1,3(2H)-dione (4.24 g) was given with a nominal yield of 71.1%. RMN-H(CDCl$_3$) MS: base peak 855.

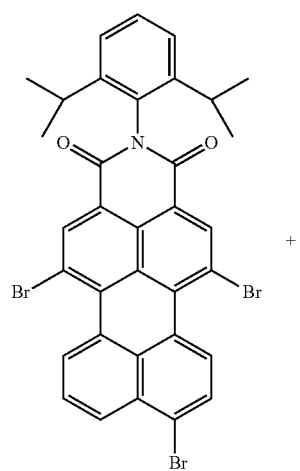

+

34

-continued

Preparation of 5,15-bis(4-(tert-butyl)phenoxy)-2-(2,6-diisopropylphenyl)-1H-thioxantheno[2',1',9':10,5,6]anthra[2,1,9-def]isoquinoline-1,3(2H)-dione Compound 8-bromo-5,12-bis(4-(tert-butyl)phenoxy)-2-(2,6-diisopropylphenyl)-1H-benzo[5,10]anthra[2,1,9-def]isoquinoline-1,3(2H)-dione (3.0 g), 2-aminobenzenthiol (0.48 g, 10% excess) and anhydrous potassium carbonate (0.24 g) were added to 30 mL of N-methyl-2-pyrrolidinone (NMP). The solution was heated rapidly and refluxed for 30 min. After a minute the liquor was added to 2% aqueous hydrochloride acid (250 ml) and after standing overnight, filtered and dried at 105° C. to give a red-blue solid of 8-((2-aminophenyl)thio)-5,12-bis(4-(tert-butyl)phenoxy)-2-(2,6-diisopropylphenyl)-1H-benzo[5,10]anthra[2,1,9-def]isoquinoline-1,3(2H)-dione (2.06 g) with a nominal yield of 60.0%. 8-((2-aminophenyl)thio)-5,12-bis(4-(tert-butyl)phenoxy)-2-(2,6-diisopropylphenyl)-1H-benzo[5,10]anthra[2,1,9-def]isoquinoline-1,3(2H)-dione (2.06 g) was dissolved in warm glacial acetic (12 mL) and concentration hydrochloride acid (1.3 mL) giving a fine suspension. The suspension was cooled to 0° C. and a solution of sodium nitrite (0.16 g) in water (3.6 mL) added and stirred continuously till clear. The prepared solution was added to a boiling solution of hydrated cupric sulphate (2.6 g) in water (60 mL) with good stirring within 1 hour. After boiling a further 1 hour, the solution was cooled, filtered and a blue-red solid was given. The solid was washed with a warm solution of sodium hydroxide (20 mL, 3%) three times and purified on Chromatography Column to eliminate by-products. The blue solid of 5,15-bis(4-(tert-butyl)phenoxy)-2-(2,6-diisopropylphenyl)-1H-thioxantheno[2',1',9':10,5,6]anthra[2,1,9-def]isoquinoline-1,3(2H)-dione (0.69 g) was given with a nominal yield of 34.2%. MS: base peak 884.

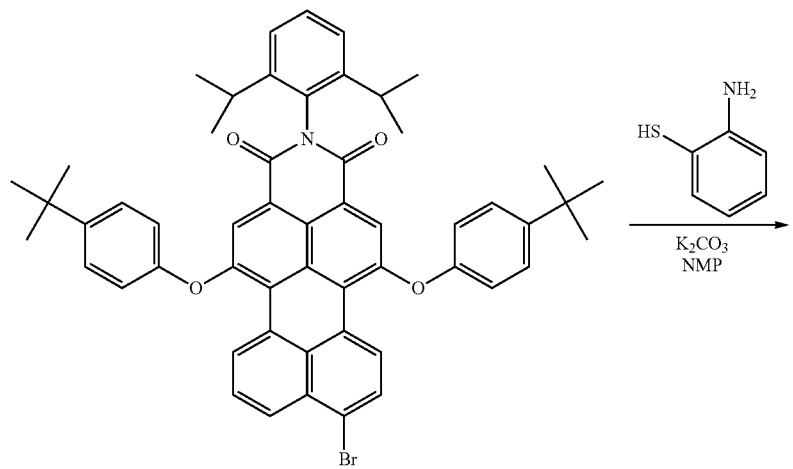
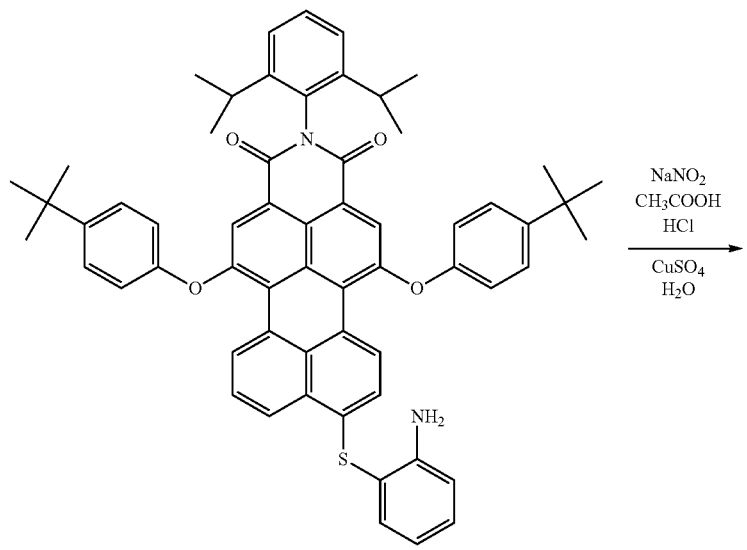
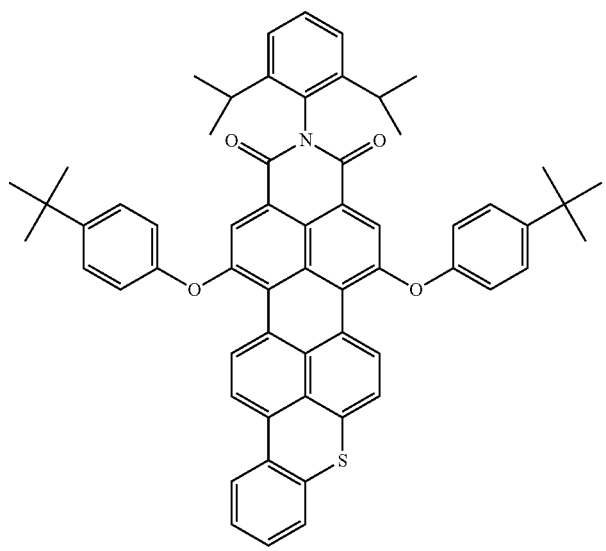

Preparation of 2-(2,6-diisopropylphenyl)-1H-thioxantheno[2',1',9':10,5,6]anthra[2,1,9-def]isoquinoline-1,3(2H)-dione Compound 8-bromo-2-(2,6-diisopropylphenyl)-1H-benzo[5,10]anthra[2,1,9-def]isoquinoline-1,3(2H)-dione (9.0 g), 2-aminobenzenthiol (2.19 g, 10% excess) and anhydrous potassium carbonate (1.10 g) were added to 100 mL of N-methyl-2-pyrrolidinone (NMP). The solution was heated rapidly and refluxed for 30 min. After a minute the liquor was added to 2% aqueous hydrochloride acid (750 ml) and after standing overnight, filtered and dried at 105° C. to give a red-blue solid of 8-((2-aminophenyl)thio)-2-(2,6-diisopropylphenyl)-1H-benzo[5,10]anthra[2,1,9-def]isoquinoline-1,3(2H)-dione (8.31 g) with a nominal yield of 86.3%. 8-((2-aminophenyl)thio)-2-(2,6-diisopropylphenyl)-1H-benzo[5,10]anthra[2,1,9-def]isoquinoline-1,3(2H)-dione (5.15 g) was dissolved in warm glacial acetic (31 mL) and concentration hydrochloride acid (3.1 mL) giving a fine suspension. The suspension was cooled to 0° C. and a solution of sodium nitrite (0.6 g) in water (9 mL) added and stirred continuously till clear. The prepared solution was added to a boiling solution of hydrated cupric sulphate (9.7 g) in water (150 mL) with good stirring within 1 hour. After boiling a further 1 hour, the solution was cooled, filtered and a blue solid was given. The solid was washed with a warm solution of sodium hydroxide (50 mL, 3%) three times and purified on chromatography column to eliminate by-products. The blue solid of 2-(2,6-diisopropylphenyl)-1H-thioxantheno[2',1',9':10,5,6]anthra[2,1,9-def]isoquinoline-1,3(2H)-dione (1.82 g) was given with a nominal yield of 36.5%. MS: base peak 587.

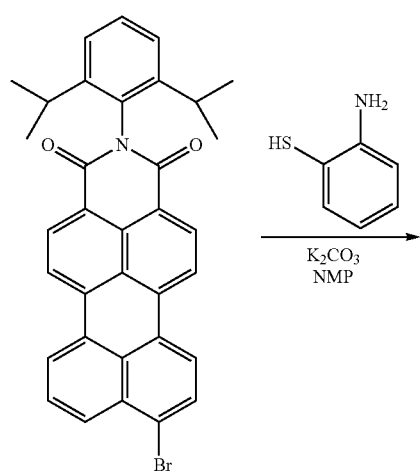

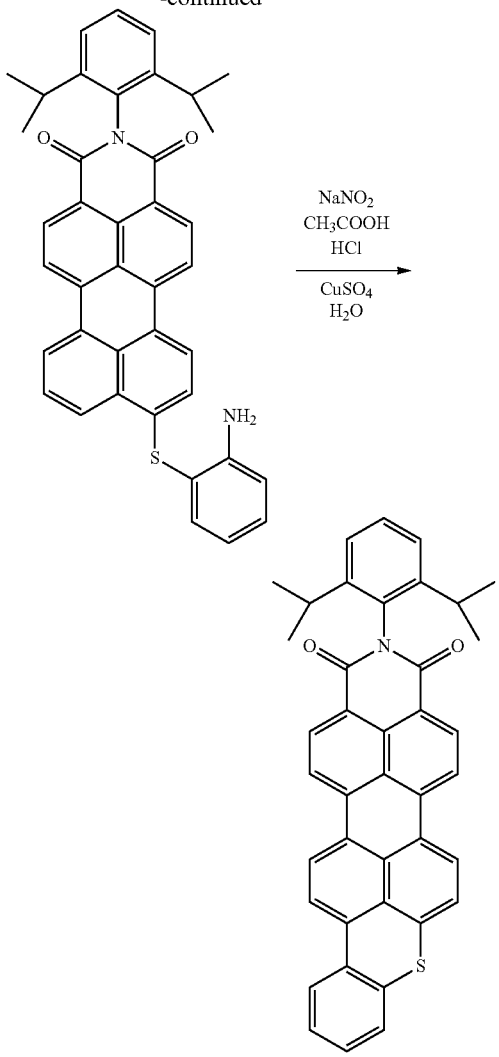

The ink according to the present invention contains at least one compound of formula (1) and/or other formulas according to the present invention. Examples of such inks which can be used may have the following formulations and are suitable to be used with inkjet printers.

Ink Formulation 1

| Component | Function | % b.w. |
|---|---|---|
| Nitrocellulose | Binder resin | 1.5 |
| Lithium Perchlorate | Salt for conductivity | 0.5 |
| 5,15-bis(4-(tert-butyl)phenoxy)-2-(2,6-diisopropylphenyl)-1H-thioxantheno[2',1',9':10,5,6]anthra[2,1,9-def]isoquinoline-1,3(2H)-dione | Dye | 1.0 |
| Acetone | Solvent | 97.0 |

The ink according to the present invention is not only based with one dye according to formula (1) and/or other formulas according to the present invention, but could also be a mixture of different dyes of formula (1) and/or the other formulas which leads to a complex ink, such as with multiple fluorescent properties, and is useful against forgery and/or counterfeiting.

It is noted that the foregoing examples have been provided merely for the purpose of explanation and are in no way to be construed as limiting of the present invention. While the present invention has been described with reference to exemplary embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A polycyclic aromatic hydrocarbon compound of general formula (1):

(P—O)$_x$-Q-Y$_w$                            (1)

wherein P represents a polymeric moiety having at least three repeating units which comprise an optionally substituted phenyl ring;

Q represents a polycyclic aromatic hydrocarbon moiety containing an S atom or S(=O)$_2$ moiety in its basic structure;

Y is selected from (i) halogen, (ii) optionally substituted N-heterocycloaliphatic groups having from 3 to about 8 ring members and which are bonded to Q through an N atom, and (iii) optionally substituted phenoxy groups;

x represents an integer of from 0 to 4; and w represents an integer of from 0 to 4 and wherein w and x are not simultaneously 0, provided that when x=0, at least one Y is selected from (ii) and (iii).

2. The compound of claim 1, wherein Q represents a moiety of formula (A) or (A'):

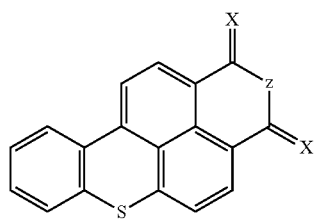
(A)

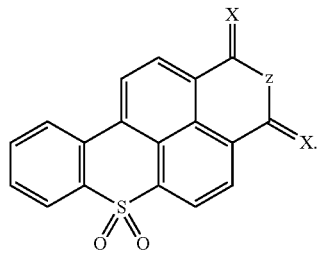
(A')

wherein Z represents O, S or N—R;
wherein X, which can be the same or different, represents O, S, or NR'; and
R and R' independently represent an optionally substituted aliphatic, cycloaliphatic, aromatic, heteroaromatic, alkylaryl, alkylheteroaryl, arylalkyl or heteroarylalkyl group having from 1 to about 20 carbon atoms; and R and R' may also be combined to form, together with the N atoms to which they are attached, an optionally substituted and/or fused 5- to 7-membered ring.

3. The compound of claim 1, wherein Q represents a moiety of formula (B) or (B'):

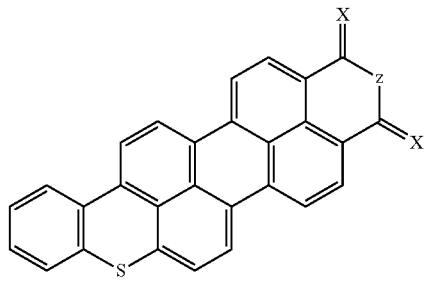
(B)

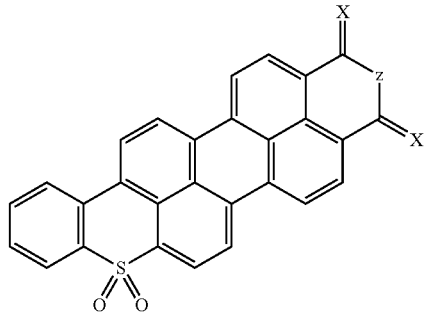
(B')

wherein Z represents O, S or N—R;
wherein X, which can be the same or different, represents O, S, or NR'; and
R and R' independently represent an optionally substituted aliphatic, cycloaliphatic, aromatic, heteroaromatic, alkylaryl, alkylheteroaryl, arylalkyl or heteroarylalkyl group having from 1 to about 20 carbon atoms; and R and R' may also be combined to form, together with the N atoms to which they are attached, an optionally substituted and/or fused 5- to 7-membered ring.

4. The compound of claim 1, wherein x is 1 and w=0.

5. The compound of claim 1, wherein x is 0 and w is 2 or not higher than 4.

6. The compound of claim 1, wherein (x+w) is not higher than about 4.

7. The compound of claim 1, wherein the compound is of formula (I) or (II) or (III) or (IV) or (V) or (VI):

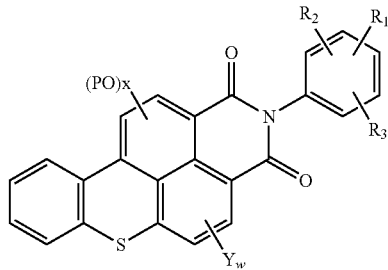
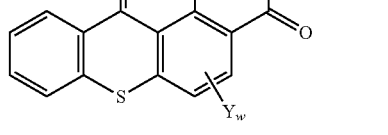
(I)

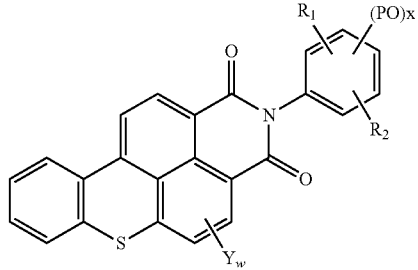
(II)

-continued

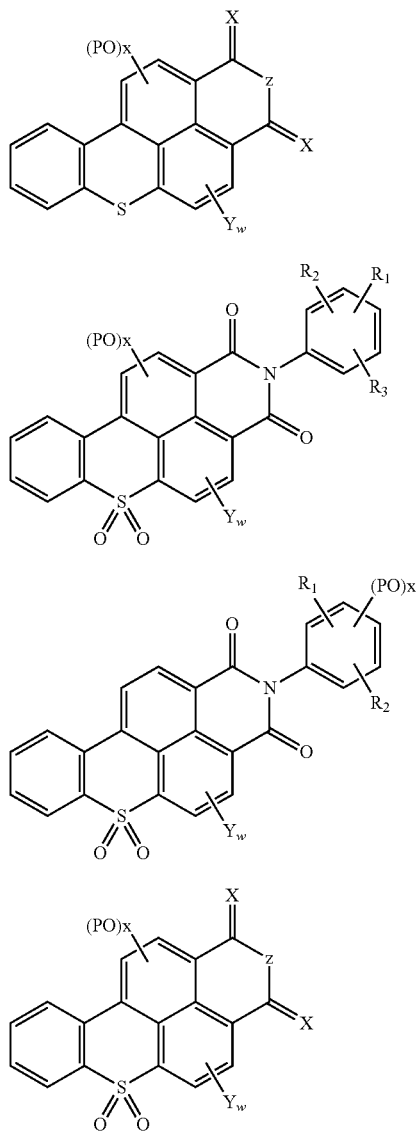

(III)

(IV)

(V)

(VI)

wherein in the case of formula (III) and (VI), Z represents O, S or N—R; and X, which can be the same or different, represents O, S, or NR'; and R and R' independently represent an optionally substituted aliphatic, cycloaliphatic, aromatic, heteroaromatic, alkylaryl, alkylheteroaryl, arylalkyl or heteroarylalkyl group having from 1 to about 20 carbon atoms; and R and R' may be combined to form, together with the N atoms to which they are attached, an optionally substituted and/or fused 5- to 7-membered ring; $R_1$, $R_2$ and $R_3$ are independently selected from hydrogen, $C_1$-$C_4$ alkyl, $C_1$-$C_4$ alkyl-COOH, $C_1$-$C_4$ alkyl-SO$_3$H, $C_1$-$C_4$ alkoxy, mono($C_1$-$C_4$)alkylamino, di($C_1$-$C_4$)alkylamino, $C_1$-$C_4$ aminoalkyl, halogen, cyano, nitro, and SO$_3$H, the alkyl groups being optionally substituted;

Y is selected from (i) halogen and (ii) optionally substituted N-heterocycloaliphatic groups having from 3 to about 8 ring members and which are bonded to an aromatic ring through an N atom, and (iii) optionally substituted phenoxy groups which are bonded to an aromatic ring through an O atom, the phenoxy group may be substituted by one or more substituents selected from halogen, nitro, cyano, NRR', SO$_3$H and COOH and salts and derivatives of these sulfonic and carboxylic acid groups, OH, heterocycloalkyl comprising up to three heteroatoms selected from O, N and S as ring members and from 3 to about 8 ring members, and alkyl (including cycloalkyl) and alkoxy (including cycloalkoxy) groups comprising from 1 to about 10 carbon atoms;

P represents a polymeric moiety having at least three repeating units which comprise an optionally substituted phenyl ring; and w is an integer of from 0 to 4.

8. The compound of claim 1, wherein the compound is a compound of one of formulae (C), (D) or (E) or (F) or (G) or (H):

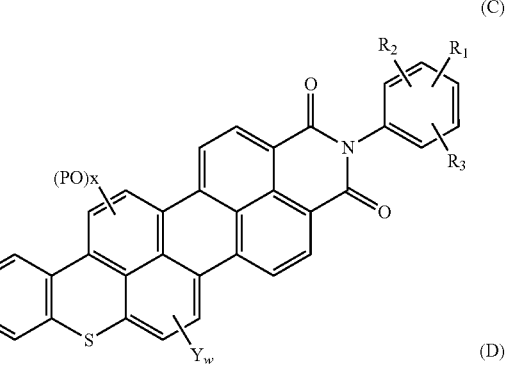

(C)

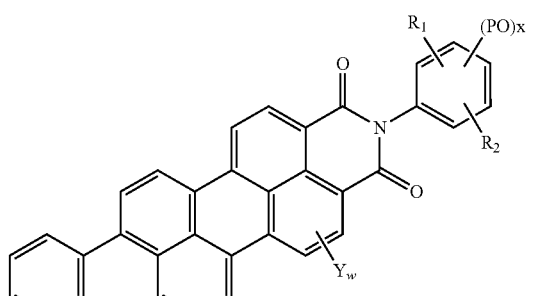

(D)

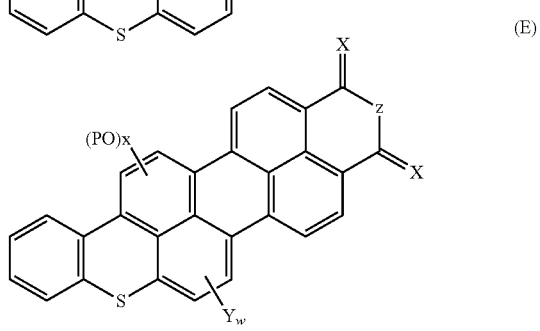

(E)

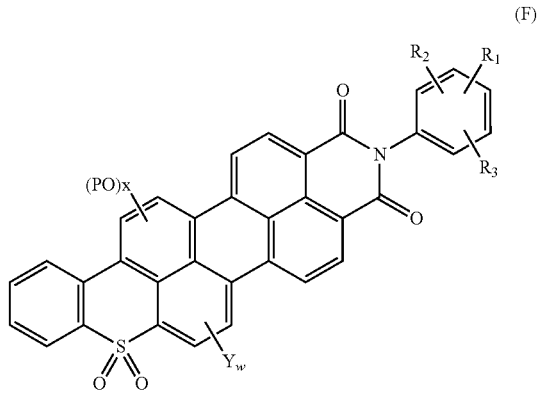

(F)

-continued

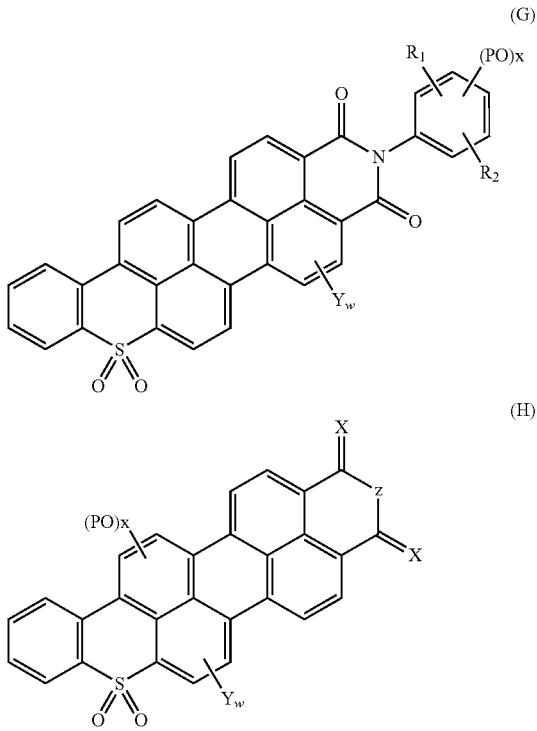

wherein in the case of formula (E) and (H), Z represents O, S or N—R; and X, which can be the same or different, represents O, S, or NR'; and R and R' independently represent an optionally substituted aliphatic, cycloaliphatic, aromatic, heteroaromatic, alkylaryl, alkylheteroaryl, arylalkyl or heteroarylalkyl group having from 1 to about 20 carbon atoms; and R and R' may be combined to form, together with the N atoms to which they are attached, an optionally substituted and/or fused 5- to 7-membered ring; $R_1$, $R_2$ and $R_3$ are independently selected from hydrogen, $C_1$-$C_4$ alkyl, $C_1$-$C_4$ alkyl-COOH, $C_1$-$C_4$ alkyl-$SO_3H$, $C_1$-$C_4$ alkoxy, mono($C_1$-$C_4$)alkylamino, di($C_1$-$C_4$)alkylamino, $C_1$-$C_4$ aminoalkyl, halogen, cyano, nitro, and $SO_3H$, the alkyl groups being optionally substituted;

Y is selected from (i) halogen and (ii) optionally substituted N-heterocycloaliphatic groups having from 3 to about 8 ring members and which are bonded to an aromatic ring through an N atom; and (iii) optionally substituted phenoxy groups which are bonded to an aromatic ring through an O atom, the phenoxy group may be substituted by one or more substituents selected from halogen, nitro, cyano, NRR', $SO_3H$ and COOH and salts and derivatives of these sulfonic and carboxylic acid groups, OH, heterocycloalkyl comprising up to three heteroatoms selected from O, N and S as ring members and from 3 to about 8 ring members, and alkyl (including cycloalkyl) and alkoxy (including cycloalkoxy) groups comprising from 1 to about 10 carbon atoms;

P represents a polymeric moiety having at least three repeating units which comprise an optionally substituted phenyl ring;

and x is an integer of from 0 to 4; and w is an integer of from 0 to 4.

9. The compound according to claim 8, wherein x is 0.

10. The compound of claim 1, wherein at least one group Y is selected from heterocycloaliphatic groups having from 3 to about 8 ring members, which ring members comprise from 1 to about 3 heteroatoms selected from N, S, and O, provided that at least one ring member is N, which heterocycloaliphatic compounds may be substituted by one or more substituents selected from alkyl and alkoxy groups each comprising up to about 10 carbon atoms.

11. The compound of claim 1, wherein at least one group Y is a residue of a heterocycloaliphatic compound selected from optionally substituted azacyclooctane, optionally substituted azepane, optionally substituted piperidine, optionally substituted piperazine, optionally substituted pyrrolidine, optionally substituted azetidine, optionally substituted aziridine, optionally substituted morpholine, optionally substituted oxazolidine, optionally substituted pyrazolidine, optionally substituted isopyrazolidine, optionally substituted isoxazolidine, and optionally substituted thiazolidine, one or more substituents each being selected from $C_1$-$C_4$ alkoxy and $C_1$-$C_6$ alkyl groups.

12. The compound of claim 1, wherein P is a residue of a polymeric compound of general formula (2):

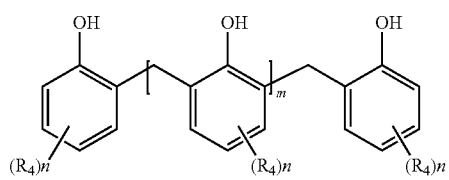

wherein the groups $R_4$, the same or different from each other, are selected from $C_1$-$C_{10}$ alkyl and $C_1$-$C_4$ alkoxy;

m represents an integer of from 1 to about 30;

n represents an integer of from 1 to about 3.

13. The compound of claim 12, wherein m represents an integer of from 1 to 10 and n is 1 or 2.

14. The compound of claim 12, wherein the groups $R_4$ are independently selected from $C_1$-$C_{10}$ alkyl.

15. The compound of claim 12, wherein the groups $R_4$ are independently selected from isopropyl, tert-butyl, tert-octyl, n-nonyl, and branched nonyl.

16. A process for making a compound of claim 1, wherein the process comprises reacting in a polar aprotic organic solvent a compound of formula Q-(Hal)$_v$ wherein Hal represents halogen and v represents an integer of from 2 to 8, successively with an N-containing cycloaliphatic compound and a polymeric compound of formula P—OH.

17. The process of claim 16 wherein at least a reaction involving the N-containing cycloaliphatic compound is carried out in the presence of at least one of an inorganic base and a strong organic non-nucleophilic base.

18. The process of claim 16, wherein from about 0.5 to about 10 g of compound of formula Q-(Hal)$_v$ are employed per 100 g of polymeric compound of formula P—OH.

19. The process of claim 16, wherein the polar solvent comprises at least one of N-methylpyrrolidone, dimethyl formamide, dimethyl acetamide, and dimethylsulfoxide.

20. The process of claim 16, wherein the process is represented as follows:

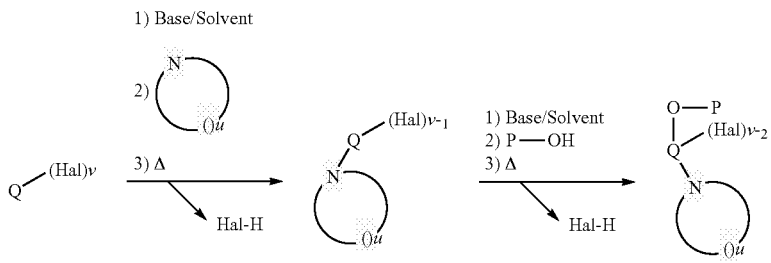

wherein
( ) represents $CH_2$ wherein at least one $CH_2$ group can be replaced by O, NH or S;
u is from 2 to 7;
v is an integer of from 2 to 8.

21. A printing ink composition, wherein the composition comprises a polar liquid medium and at least one compound of claim 1 dissolved or dispersed in the medium.

22. The printing ink composition of claim 21, wherein the composition comprises from about 0.01% to about 40% by weight of the at least one compound, based on a total weight of the composition.

23. The printing ink composition of claim 21, wherein the printing ink composition further comprises at least one conductivity imparting substance.

24. A marking or security feature which is made with the printing ink composition of claim 21.

25. A marking or security feature which comprises at least one compound of claim 1.

26. The marking or security feature of claim 24, wherein the marking or security feature comprises at least one of a thread, a label, a barcode, a 2D code, a pattern, indicia, and a data matrix.

27. An article which comprises the marking or security feature of claim 24.

28. The article of claim 27, wherein the marking or security feature is present as a layer on the article.

29. The article of claim 27, wherein the article is at least one of a can, a metal, an aluminum foil, a cartridge, a capsule, an article made of glass, an article made of ceramic, a packaging, a banknote, a passport, a security document, a value document, a ticket, a thread, a label, a card, a commercial good, and a cigarette packaging which may or may not carry coded or encrypted information.

30. A method of authenticating an article, wherein the method comprises providing the article with the marking or security feature of claim 24.

31. A method of authenticating an article, wherein the method comprises applying onto the article the printing ink composition of claim 21.

32. The method of claim 30, wherein the article is at least one of a can, a metal, an aluminum foil, a cartridge, a capsule, an article made of glass, an article made of ceramic, a packaging, a banknote, a passport, a security document, a value document, a ticket, a thread, a label, a card, a commercial good, and a cigarette packaging which may or may not carry coded or encrypted information.

* * * * *